(12) United States Patent
Abe et al.

(10) Patent No.: US 9,647,294 B2
(45) Date of Patent: May 9, 2017

(54) NON-AQUEOUS ELECTROLYTIC SOLUTION, ELECTROCHEMICAL ELEMENT USING SAME, AND ALKYNYL COMPOUND USED THEREFOR

(75) Inventors: Koji Abe, Yamaguchi (JP); Kazuhiro Miyoshi, Yamaguchi (JP); Masahide Kondo, Yamaguchi (JP)

(73) Assignee: UBE INDUSTRIES, LTD., Ube-shi (JP)

( * ) Notice: Subject to any disclaimer, the term of this patent is extended or adjusted under 35 U.S.C. 154(b) by 691 days.

(21) Appl. No.: 13/576,182

(22) PCT Filed: Feb. 2, 2011

(86) PCT No.: PCT/JP2011/052177
§ 371 (c)(1),
(2), (4) Date: Jul. 31, 2012

(87) PCT Pub. No.: WO2011/096450
PCT Pub. Date: Aug. 11, 2011

(65) Prior Publication Data
US 2012/0301797 A1    Nov. 29, 2012

(30) Foreign Application Priority Data

Feb. 3, 2010   (JP) ................................ 2010-022461
Mar. 31, 2010  (JP) ................................ 2010-082495

(51) Int. Cl.
| H01M 10/056 | (2010.01) |
| C07C 309/70 | (2006.01) |
| C07C 309/68 | (2006.01) |
| C07C 309/67 | (2006.01) |
| H01M 10/0567 | (2010.01) |
| H01M 10/052 | (2010.01) |
| C07F 9/113 | (2006.01) |
| C07F 9/32 | (2006.01) |

(52) U.S. Cl.
CPC ....... *H01M 10/0567* (2013.01); *C07C 309/67* (2013.01); *C07F 9/113* (2013.01); *C07F 9/327* (2013.01); *H01M 10/052* (2013.01); *H01M 2300/0025* (2013.01); *Y02E 60/122* (2013.01); *Y02T 10/7011* (2013.01)

(58) Field of Classification Search
None
See application file for complete search history.

(56) References Cited

U.S. PATENT DOCUMENTS

| 4,259,350 A | 3/1981 | Morisawa et al. |
| 6,479,191 B1 | 11/2002 | Hamamoto et al. |
| 7,727,677 B2 * | 6/2010 | Abe ................ H01M 10/0525 429/188 |
| 2001/0006751 A1 | 7/2001 | Gan et al. |
| 2002/0076619 A1 * | 6/2002 | Yamada .............. H01M 10/052 429/324 |
| 2007/0231707 A1 | 10/2007 | Abe et al. |
| 2008/0038644 A1 * | 2/2008 | Abe ................... H01M 10/0525 429/331 |
| 2011/0045361 A1 | 2/2011 | Abe et al. |

FOREIGN PATENT DOCUMENTS

| EP | 1 772 924 A1 | 4/2007 |
| JP | 54 122727 | 9/1979 |
| JP | 2000-195545 A | 7/2000 |
| JP | 2009-152133 A | 7/2009 |
| WO | WO 2005/099023 A1 | 10/2005 |
| WO | 2005 117197 | 12/2005 |
| WO | WO 2009/122908 A1 | 10/2009 |
| WO | WO 2011/096450 A1 | 8/2011 |

OTHER PUBLICATIONS

Le Flohic, A., et al., "Unsaturated Sultones from Unsaturated Sulfonates: Synthesis by Ring-Closing Metathesis and Reactivity," Synlett, No. 5, pp. 667-670, (2003).
International Search Report Issued Apr. 26, 2011 in PCT/JP11/52177 Filed Feb. 2, 2011.
Extended European Search Report issued on Jun. 30, 2014 in the corresponding European Application No. 11739798.4.
Partial European Search Report issued May 6, 2015 in Patent Application No. 15150250.7.

(Continued)

*Primary Examiner* — Barbara Gilliam
*Assistant Examiner* — Adam A Arciero
(74) *Attorney, Agent, or Firm* — Oblon, McClelland, Maier & Neustadt, L.L.P.

(57) ABSTRACT

The present invention provides an excellent nonaqueous electrolytic solution capable of improving low-temperature and high-temperature cycle properties and load characteristics after high-temperature charging storage, an electrochemical element using it, and an alkynyl compound used for it.

The nonaqueous electrolytic solution of the present invention comprises containing at least one alkynyl compound represented by the following general formula (I) in an amount of from 0.01 to 10% by mass in the nonaqueous electrolytic solution.

$$R^1(O)_n-X^1-R^2 \quad (I)$$

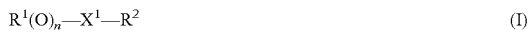

(In the formula, $X^1$ represents a group —C(=O)—, a group —C(=O)—C(=O)—, a group —S(=O)$_2$—, a group —P(=O) (—R$^3$)—, or a group —X$^3$—S(=O)$_2$O—. $R^1$ represents an alkenyl group, a formyl group, an alkyl group, an acyl group, an arylcarbonyl, an alkanesulfonyl group, an alkynyloxysulfonyl group, an arylsulfonyl group, a dialkylphosphoryl group, an alkyl(alkoxy)phosphoryl group, or a dialkoxyphosphoryl group; $R^2$ represents an alkynyl group or an alkynyloxy group; $R^3$ represents an alkyl group, an alkenyl group, an alkynyl group, an aryl group, an alkoxy group, an alkenyloxy group, an alkynyloxy group, or an aryloxy group; n indicates 0 or 1.

20 Claims, No Drawings

(56) References Cited

OTHER PUBLICATIONS

Koji Abe, et al., "Functional Electrolytes—Triple-Bonded Compound as an Additive for Negative Electrode" Journal of the Electrochemical Society, vol. 154, No. 8, XP002699187, Jun. 22, 2007, pp. A810-A815.
Office Action issued May 10, 2016 in Japanese Patent Application No. 2015-078463.
Extended European Search Report issued Aug. 24, 2015 in Patent Application No. 15150250.7.

* cited by examiner

NON-AQUEOUS ELECTROLYTIC SOLUTION, ELECTROCHEMICAL ELEMENT USING SAME, AND ALKYNYL COMPOUND USED THEREFOR

TECHNICAL FIELD

The present invention relates to a nonaqueous electrolytic solution, an electrochemical element using it, and a novel alkynyl compound used for electrochemical elements, etc.

BACKGROUND ART

In recent years, lithium secondary batteries have been widely used as power supplies for small-sized electronic devices such as mobile telephones, notebook-size personal computers and the like, power supplies for electric vehicles, as well as for electric power storage, etc. These electronic devices and vehicles may be used in a broad temperature range, for example, at midsummer high temperatures or at frigid low temperatures, and are therefore required to be improved in point of the battery performance such as well-balanced cycle properties and/or high-temperature charging storage properties in a broad temperature range.

A lithium secondary battery is mainly constituted of a positive electrode and a negative electrode containing a material capable of absorbing and releasing lithium, and a nonaqueous electrolytic solution containing a lithium salt and a nonaqueous solvent. For the nonaqueous solvent, used are carbonates such as ethylene carbonate (EC), propylene carbonate (PC), etc.

As the negative electrode, known are metal lithium, and metal compounds (metal elemental substances, oxides, alloys with lithium, etc.) and carbon materials capable of absorbing and releasing lithium. In particular, a lithium secondary battery using a carbon material capable of absorbing and releasing lithium, such as coke, artificial graphite, natural graphite or the like, has been widely put into practical use.

For example, it is known that, in a lithium secondary battery using a highly-crystalline carbon material such as natural graphite, artificial graphite or the like as the negative electrode material therein, the decomposed product or gas generated through reductive decomposition of the solvent in the nonaqueous electrolytic solution on the surface of the negative electrode during charging detracts from the electrochemical reaction favorable for the battery, therefore worsening the cycle properties and/or the high-temperature charging storage properties of the battery. Deposition of the decomposed product of the nonaqueous solvent interferes with smooth absorption and release of lithium by the negative electrode, and therefore, in particular, the cycle properties at low temperatures and high temperatures and/or the load characteristics after high-temperature charging storage may be thereby often worsened.

In addition, it is known that a lithium secondary battery using a lithium metal or its alloy, or a metal elemental substance such as tin, silicon or the like or its metal oxide as the negative electrode material therein may have a high initial battery capacity but its battery performance such as cycle properties and/or load characteristics after high-temperature charging storage greatly worsens, since the micronized powdering of the material is promoted during cycles thereby bringing about accelerated reductive decomposition of the nonaqueous solvent, as compared with the negative electrode of a carbon material. In addition, the micronized powdering of the negative electrode material and the deposition of the decomposed product of the nonaqueous solvent may interfere with smooth absorption and release of lithium by the negative electrode, and therefore, in particular, the cycle properties at low temperatures and at high temperatures may be thereby often worsened.

On the other hand, it is known that, in a lithium secondary battery using, for example, $LiCoO_2$, $LiMn_2O_4$, $LiNiO_2$ or $LiFePO_4$ as the positive electrode, when the nonaqueous solvent in the nonaqueous electrolytic solution is heated at a high temperature in the charged state, the decomposed product or the gas thereby locally generated through partial oxidative decomposition in the interface between the positive electrode material and the nonaqueous electrolytic solution interferes with the electrochemical reaction favorable for the battery, and therefore the battery performance such as cycle properties and/or load characteristics after high-temperature charging storage is thereby also worsened.

As in the above, the decomposed product and the gas generated through decomposition of the nonaqueous electrolytic solution on the positive electrode or the negative electrode may interfere with the movement of lithium ions or may swell the battery, and the battery performance is thereby worsened. Despite the situation, electronic appliances equipped with lithium secondary batteries therein are offering more and more an increasing range of functions and are being in a stream of further increase in power consumption. With that, the capacity of lithium secondary batteries is being much increased, and the space volume for the nonaqueous electrolytic solution in the battery is decreased by increasing the density of the electrode and by reducing the useless space volume in the battery. Accordingly, the situation is that even decomposition of only a small amount of the nonaqueous electrolytic solution may worsen the battery performance such as cycle properties at low temperatures and high temperatures and/or load characteristics after high-temperature charging storage.

As a lithium primary battery, for example, known is one in which the positive electrode is formed of manganese dioxide or fluorographite and the negative electrode is formed of lithium metal, and the lithium primary battery of the type is widely used as having a high energy density, for which, however, it is desired to prevent the increase in the internal resistance and to improve the low-temperature and high-temperature cycle properties, and to prevent the increase in the internal resistance during long-term storage to thereby improve the long-term storability at high temperatures.

Recently, further, as a novel power source for electric vehicles or hybrid electric vehicles, electric storage devices have been developed, for example, an electric double layer capacitor using activated carbon or the like as the electrode from the viewpoint of the output density thereof, and a hybrid capacitor including a combination of the electric storage principle of a lithium ion secondary battery and that of an electric double layer capacitor (an asymmetric capacitor where both the capacity by lithium absorption and release and the electric double layer capacity are utilized) from the viewpoint of both the energy density and the output density thereof; and it is desired to improve the battery performance such as the cycle properties at low temperatures and high temperatures and/or the load characteristics after high-temperature charging storage of these capacitors.

Patent Reference 1 discloses a lithium ion secondary battery using an electrolytic solution that contains a carbonate compound having both a carbon-carbon triple bond and a non-aromatic carbon-carbon double bond in the molecule, saying that the battery is excellent in cycle properties and high-temperature storage properties.

Patent Reference 2 discloses a lithium ion secondary battery, in which 2-butyne-1,4-diol dimethanesulfonate is added to the electrolytic solution in an amount of 1% by weight of the solution, saying that the cycle properties of the battery at 20° C. are thereby improved.

CITATION LIST

Patent References

Patent Reference 1: JP-A 2009-193836
Patent Reference 2: JP-A 2000-195545

DISCLOSURE OF THE INVENTION

Problems that the Invention is to Solve

An object of the present invention is to provide an excellent nonaqueous electrolytic solution capable of improving low-temperature and high-temperature cycle properties and load characteristics after high-temperature charging storage, an electrochemical element using it, and an alkynyl compound used for it.

Means for Solving the Problems

The present inventors have investigated in detail the performance of the nonaqueous electrolytic solutions in the above-mentioned prior art. As a result, the actual situation is that the nonaqueous electrolytic solution in the Patent Reference 1 and others could not obtain good cycle properties in a broad range of low temperatures and high temperatures. In addition, the actual situation is that the nonaqueous electrolytic solution in Patent Reference 2 and others could not sufficiently satisfy the load characteristics after high-temperature charging storage.

Given the situation, the present inventors have assiduously studied for the purpose of solving the above-mentioned problems, and have found that, when an alkynyl compound having a specific structure of bonding the alkynyl group to the compound via a specific group is added to a nonaqueous electrolytic solution, then the electrolytic solution can improve cycle properties at low temperatures and high temperatures and load characteristics after high-temperature charging storage, and have completed the present invention.

Specifically, the present invention provides the following (1) to (5):

(1) A nonaqueous electrolytic solution of an electrolyte salt dissolved in a nonaqueous solvent, which comprises at least one alkynyl compound represented by the following general formula (I) in an amount of from 0.01 to 10% by mass of the nonaqueous electrolytic solution:

[Chemical Formula 1]

(In the formula, $X^1$ represents a group —C(=O)—, a group —C(=O)—C(=O)—, a group —S(=O)$_2$—, a group —P(=O) (—R$^3$)—, or a group —X$^3$—S(=O)$_2$O— (where X$^3$ represents an alkylene group having from 1 to 8 carbon atoms, or a divalent linking group having from 2 to 8 carbon atoms and containing at least one ether bond); R$^1$ represents an alkenyl group having from 2 to 8 carbon atoms, a formyl group, an alkyl group having from 1 to 8 carbon atoms, an acyl group having from 2 to 8 carbon atoms, an arylcarbonyl group having from 7 to 15 carbon atoms, an alkanesulfonyl group having from 1 to 8 carbon atoms, an alkynyloxysulfonyl group having from 3 to 8 carbon atoms, an arylsulfonyl group having from 6 to 15 carbon atoms, a dialkylphosphoryl group having from 2 to 16 carbon atoms, an alkyl(alkoxy)phosphoryl group having from 2 to 16 carbon atoms, or a dialkoxyphosphoryl group having from 2 to 16 carbon atoms; R$^2$ represents an alkynyl group having from 3 to 8 carbon atoms, or an alkynyloxy group having from 3 to 8 carbon atoms; R$^3$ represents an alkyl group having from 1 to 8 carbon atoms, an alkenyl group having from 2 to 8 carbon atoms, an alkynyl group having from 3 to 8 carbon atoms, an aryl group having from 6 to 18 carbon atoms, an alkoxy group having from 1 to 8 carbon atoms, an alkenyloxy group having from 2 to 8 carbon atoms, an alkynyloxy group having from 3 to 8 carbon atoms, or an aryloxy group having from 6 to 18 carbon atoms; n indicates 0 or 1; provided that when $X^1$ is a group —C(=O)—, then n is 1, R$^1$ is an alkenyl group having from 2 to 8 carbon atoms, and R$^2$ is an alkynyl group having from 3 to 8 carbon atoms, when $X^1$ is a group —C(=O)—C(=O)—, a group —S(=O)$_2$—, or a group —P(=O) (—R$^3$)—, then n is 1, R$^1$ is an alkenyl group having from 2 to 8 carbon atoms, and R$^2$ is an alkynyloxy group having from 3 to 8 carbon atoms, and when $X^1$ is a group —X$^3$—S(=O)$_2$O—, then R$^2$ is an alkynyl group having from 3 to 8 carbon atoms).

(2) The nonaqueous electrolytic solution of the above (1), wherein the alkynyl compound represented by the general formula (I) is an alkynyl sulfonate compound represented by the following general formula (III):

[Chemical Formula 2]

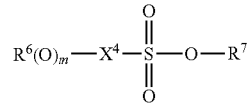

(In the formula, X$^4$ represents an alkylene group having from 1 to 8 carbon atoms, or a divalent linking group having from 2 to 8 carbon atoms and containing at least one ether bond; R$^6$ represents a formyl group, an alkyl group having from 1 to 8 carbon atoms, an acyl group having from 2 to 8 carbon atoms, an arylcarbonyl group having from 7 to 15 carbon atoms, an alkanesulfonyl group having from 1 to 8 carbon atoms, an alkynyloxysulfonyl group having from 3 to 8 carbon atoms, an arylsulfonyl group having from 6 to 15 carbon atoms, a dialkylphosphoryl group having from 2 to 16 carbon atoms, an alkyl(alkoxy)phosphoryl group having from 2 to 16 carbon atoms, or a dialkoxyphosphoryl group having from 2 to 16 carbon atoms; R$^7$ represents an alkynyl group having from 3 to 8 carbon atoms; m indicates 0 or 1; provided that when m is 1, then R$^6$ is a formyl group, an alkyl group having from 1 to 8 carbon atoms, an acyl group having from 2 to 8 carbon atoms, an arylcarbonyl group having from 7 to 15 carbon atoms, an alkanesulfonyl group having from 1 to 8 carbon atoms, an arylsulfonyl group having from 6 to 15 carbon atoms, a dialkylphosphoryl group having from 2 to 16 carbon atoms, an alkyl(alkoxy) phosphoryl group having from 2 to 16 carbon atoms, or a dialkoxyphosphoryl group having from 2 to 16 carbon atoms; at least one hydrogen atom on the carbon atom of R$^6$, X$^4$ and R$^7$ may be substituted with a halogen atom).

(3) An electrochemical element comprising a positive electrode, a negative electrode, and a nonaqueous electrolytic solution of an electrolyte salt dissolved in a nonaqueous solvent, wherein the nonaqueous electrolytic solution comprises at least one alkynyl compound represented by the above-mentioned general formula (I) in an amount of from 0.01 to 10% by mass of the nonaqueous electrolytic solution.

(4) An alkynyl compound represented by the following general formula (II):

[Chemical Formula 3]

$$R^4—X^2—R^5 \quad (II)$$

(In the formula, $X^2$ represents a group $—S(=O)_2—$, or a group $—X^3—S(=O)_2O—$ (where $X^3$ represents an alkylene group having from 1 to 8 carbon atoms, or a divalent linking group having from 2 to 8 carbon atoms and containing at least one ether bond). $R^4$ represents an alkenyl group having from 2 to 8 carbon atoms or an alkenyloxy group having from 2 to 8 carbon atoms; and $R^5$ represents an alkynyl group having from 3 to 8 carbon atoms, or an alkynyloxy group having from 3 to 8 carbon atoms.)

(5) An alkynyl sulfonate compound represented by the following general formula (III):

[Chemical Formula 4]

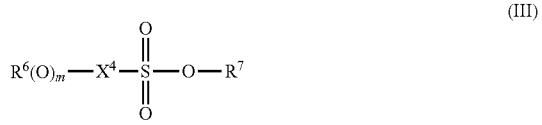

(III)

(In the formula, $X^4$, $R^6$ and $R^7$ have the same meanings as mentioned above.)

Advantage of the Invention

According to the present invention, there are provided an excellent nonaqueous electrolytic solution capable of improving battery performance such as low-temperature and high-temperature cycle properties and load characteristics after high-temperature charging storage, an electrochemical element using it, and an alkynyl compound used for it.

BEST MODE FOR CARRYING OUT THE INVENTION

[Nonaqueous Electrolytic Solution]

The nonaqueous electrolytic solution of the present invention comprises an electrolyte salt dissolved in a nonaqueous solvent, and comprises at least one alkynyl compound represented by the following general formula (I) in an amount of from 0.01 to 10% by mass of the nonaqueous electrolytic solution:

[Chemical Formula 5]

$$R^1(O)_n—X^1—R^2 \quad (I)$$

(In the formula, $X^1$, $R^1$, $R^2$ and n have the same meanings as mentioned above.)

The nonaqueous electrolytic solution of the present invention can improve battery performance such as low-temperature and high-temperature cycle properties and load characteristics after high-temperature charging storage. Though not clear, the reason may be considered as follows:

The alkynyl compound represented by the general formula (I) in the present invention has a specific electron-attracting group and a carbon-carbon triple bond-containing group, and further has still another functional group, and is therefore considered to form a low-resistance surface film having high heat resistance and to specifically improve low-temperature and high-temperature cycle properties and load characteristics after high-temperature charging storage.

In the alkynyl compound represented by the general formula (I) in the present invention, in case where $X^1$ is a group $—C(=O)—$, a group $—C(=O)—C(=O)—$, a group $—S(=O)_2—$ or a group $—P(=O)(—R^3)—$, the compound has a structure in which the unsaturated bond or ether bond-containing group bonds to the carbon-carbon triple bond-containing group (alkynyl group or alkynyloxy group) via the above-mentioned specific functional group therebetween, and in this, therefore, it is considered that the reductive decomposition at the two multiple bond sites would go on more easily. As a result, a good mixture surface film that could not be expected in the case where the carbonate compound described in Patent Reference 1 is used could be formed to exhibit the effect of specifically improving the above-mentioned battery performance.

Above all, it has been confirmed that, in the case where $X^1$ is a group $—S(=O)_2—$, an especially good mixture surface film can be formed to enhance the effect of improving the low-temperature and high-temperature cycle properties and the load characteristics after high-temperature charging storage. This is considered because the electron attractivity of the group $—S(=O)_2—$ could further promote the reductive decomposition at the multiple bond sites to thereby facilitate the formation of the polymerization surface film derived from the above-mentioned multiple bonds.

Also in the case where the alkynyl compound represented by the general formula (I) is an alkynyl sulfonate compound represented by the following general formula (III), the low-temperature and high-temperature cycle properties and the load characteristics after high-temperature charging storage can be improved, like in the above.

[Chemical Formula 6]

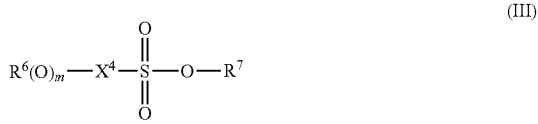

(III)

(In the formula, $X^4$, $R^6$ and $R^7$ have the same meanings as mentioned above.)

Though not clear, the reason why the nonaqueous electrolytic solution containing the alkynyl sulfonate compound represented by the general formula (III) can improve the low-temperature and high-temperature cycle properties and the load characteristics after high-temperature charging storage may be considered as follows:

Specifically, in the alkynyl sulfonate compound represented by the general formula (III), two different substituents of one specific substituent selected from an ether group ($—O—$), a formyl group ($—C(=O)H$), an acyl group ($—C(=O)R$), a sulfonyl group ($—S(=O)_2R$) and a phosphoryl group ($—P(=O)RR'$), and a triple bond-having specific sulfonate group ($—S(=O)_2OR^7$) are bonded to each other via a hydrocarbon group optionally containing an oxygen atom at the terminal and/or in the intermediate thereof, and therefore the compound has a reduction potential quite different from that of the compound of 2-butyne-1,4-diol dimethanesulfonate having a triple bond in the linking chain to link the two substituents therein, as described in Patent Reference 2. The alkynyl sulfonate compound represented by the general formula (III) has the triple bond-having specific sulfonate group (—S(=O)$_2$OR$^7$) at the terminal thereof, and therefore the surface film containing the component derived from the above-mentioned two substituents is not formed excessively on the electrode, and consequently, it may be considered that a low-resistance surface film having high heat resistance that could not be expected in the case where the compound described in Patent Reference 2 is used can be formed to exhibit the effect of specifically improving the low-temperature and high-temperature cycle properties and the load characteristics after high-temperature charging storage.

(Alkynyl Compound Represented by General Formula (I))

[Chemical Formula 7]

(I)

In the general formula (I), X$^1$ represents a group —C(=O)—, a group —C(=O)—C(=O)—, a group —S(=O)$_2$—, a group —P(=O)(—R$^3$)— or a group —X$^3$—S(=O)$_2$O— (where X$^3$ represents an alkylene group having from 1 to 8 carbon atoms, or a divalent linking group having from 2 to 8 carbon atoms and containing at least one ether bond).

In the group —X$^3$—S(=O)$_2$O—, the alkylene group having from 1 to 8 carbon atoms of X$^3$ is preferably an alkylene group having from 1 to 4 carbon atoms, more preferably from 1 to 3 carbon atoms, even more preferably 2 or 3 carbon atoms, and is especially preferably an alkylene group having 2 carbon atoms. The divalent linking group having from 2 to 8 carbon atoms and containing at least one ether bond is preferably —CH$_2$OCH$_2$—, —C$_2$H$_4$OC$_2$H$_4$—, or —C$_2$H$_4$OC$_2$H$_4$OC$_2$H$_4$—, more preferably —C$_2$H$_4$OC$_2$H$_4$—.

The alkylene group having from 1 to 8 carbon atoms, or the divalent linking group having from 2 to 8 carbon atoms and containing at least one ether bond of X$^3$ is described in detail in the section of the alkynyl sulfonate compound represented by the general formula (III) to be mentioned below.

In the general formula (I), for the linear or branched alkenyl group having from 2 to 8 carbon atoms represented by R$^1$, preferably mentioned are a linear alkenyl group such as a vinyl group, a 2-propenyl group, a 2-butenyl group, a 3-butenyl group, a 4-pentenyl group, a 5-hexenyl group, etc.; and a branched alkenyl group such as a 1-methyl-2-propenyl group, a 1-methyl-2-butenyl group, a 1,1-dimethyl-2-propenyl group, etc.

Of those, as the alkenyl group represented by R$^1$, preferred are a vinyl group, a 2-propenyl group, a 2-butenyl group, a 3-butenyl group, a 1-methyl-2-propenyl group and a 1,1-dimethyl-2-propenyl group; more preferred are a vinyl group, a 2-propenyl group and a 3-butenyl group; and even more preferred are a vinyl group and a 2-propenyl group.

In the general formula (I), the formyl group, the alkyl group having from 1 to 8 carbon atoms, the acyl group having from 2 to 8 carbon atoms, the arylcarbonyl group having from 7 to 15 carbon atoms, the alkanesulfonyl group having from 1 to 8 carbon atoms, the alkynyloxysulfonyl group having from 3 to 8 carbon atoms, the arylsulfonyl group having from 6 to 15 carbon atoms, the dialkylphosphoryl group having from 2 to 16 carbon atoms, the alkyl(alkoxy)phosphoryl group having from 2 to 16 carbon atoms and the dialkoxyphosphoryl group having from 2 to 16 carbon atoms represented by R$^2$ are described in detail in the section of the alkynyl sulfonate compound represented by the general formula (III) to be mentioned below.

In the general formula (I), for the linear or branched alkynyl group having from 3 to 8 carbon atoms represented by R$^2$, preferably mentioned are a linear alkynyl group such as a 2-propynyl group, a 2-butynyl group, a 3-butynyl group, a 4-pentynyl group, a 5-hexynyl group, etc.; and a branched alkynyl group such as a 1-methyl-2-propynyl group, a 1-methyl-2-butynyl group, a 1,1-dimethyl-2-propynyl group, etc.

Of those, as the alkynyl group represented by R$^2$, preferred is an alkynyl group having from 3 to 5 carbon atoms; more preferred are a 2-propynyl group, a 3-butynyl group, a 1-methyl-2-propynyl group and a 1,1-dimethyl-2-propynyl group; and especially preferred are a 2-propynyl group and a 1,1-dimethyl-2-propynyl group.

In the general formula (I), for the linear or branched alkynyloxy group having from 3 to 8 carbon atoms represented by R$^2$, preferably mentioned are a linear alkynyloxy group such as a 2-propynyloxy group, a 2-butynyloxy group, a 3-butynyloxy group, a 4-pentynyloxy group, a 5-hexynyloxy group, etc.; and a branched alkynyloxy group such as a 1-methyl-2-propynyloxy group, a 1-methyl-2-butynyloxy group, 1,1-dimethyl-2-propynyloxy group, etc.

Of those, as the alkynyloxy group represented by R$^2$, preferred is an alkynyloxy group having from 3 to 5 carbon atoms; more preferred are a 2-propynyloxy group, a 3-butynyloxy group, a 1-methyl-2-butynyloxy group, and a 1,1-dimethyl-2-propynyloxy group; and especially preferred are a 2-propynyloxy group and a 1,1-dimethyl-2-propynyloxy group.

In the general formula (I), for the linear or branched alkyl group having from 1 to 8 carbon atoms represented by R$^3$, preferably mentioned are a linear alkyl group such as a methyl group, an ethyl group, a propyl group, a butyl group, a pentyl group, a hexyl group, etc.; and a branched alkyl group such as an isopropyl group, a sec-butyl group, a tert-butyl group, a tert-pentyl group, etc.

Of those, as the alkyl group represented by R$^3$, preferred are a methyl group and an ethyl group, and more preferred is a methyl group.

In the general formula (I), for the linear or branched alkenyl group having from 2 to 8 carbon atoms represented by R$^3$, preferably mentioned are a linear alkenyl group such as a vinyl group, a 2-propenyl group, a 2-butenyl group, a 3-butenyl group, a 4-pentenyl group, a 5-hexenyl group, etc.; and a branched alkenyl group such as a 1-methyl-2-propenyl group, a 1-methyl-2-butenyl group, a 1,1-dimethyl-2-propenyl group, etc.

Of those, as the alkenyl group represented by R$^3$, preferred are a vinyl group, a 2-propenyl group, a 2-butenyl group, a 3-butenyl group, a 1-methyl-2-propenyl group, and a 1,1-dimethyl-2-propenyl group; more preferred are a vinyl group, a 2-propenyl group and a 3-butenyl group; and most preferred are a vinyl group and a 2-propenyl group.

In the general formula (I), for the linear or branched alkynyl group having from 3 to 8 carbon atoms represented by R$^3$, preferably mentioned are a linear alkynyl group such as a 2-propynyl group, a 2-butynyl group, a 3-butynyl group, a 4-pentynyl group, a 5-hexynyl group, etc.; and a branched alkynyl group such as a 1-methyl-2-propynyl group, a 1-methyl-2-butynyl group, a 1,1-dimethyl-2-propynyl group, etc.

Of those, as the alkynyl group represented by R$^3$, preferred is an alkynyl group having from 3 to 5 carbon atoms;

more preferred are a 2-propynyl group, a 3-butynyl group, a 1-methyl-2-propynyl group, and a 1,1-dimethyl-2-propynyl group; and more preferred are a 2-propynyl group and a 1,1-dimethyl-2-propynyl group.

In the general formula (I), for the aryl group having from 6 to 18 carbon atoms represented by $R^3$, preferably mentioned are a phenyl group, a tolyl group, a xylyl group, and a naphthyl group.

Of those, as the aryl group represented by $R^3$, preferred are a phenyl group and a tolyl group; and more preferred is a phenyl group.

In the general formula (I), for the linear or branched alkoxy group having from 1 to 8 carbon atoms represented by $R^3$, preferably mentioned a linear alkoxy group such as a methoxy group, an ethoxy group, a propoxy group, a butoxy group, a pentyloxy group, a hexyloxy group, etc.; and a branched alkoxy group such as an isopropyloxy group, a sec-butyloxy group, a tert-butyloxy group, a tert-pentyloxy group, etc.

Of those, as the alkoxy group represented by $R^3$, preferred are a methoxy group and an ethoxy group; and more preferred is an ethoxy group.

In the general formula (I), for the linear or branched alkenyloxy group having from 2 to 8 carbon atoms represented by $R^3$, preferably mentioned are a linear alkenyloxy group such as a vinyloxy group, a 2-propenyloxy group, a 2-butenyloxy group, a 3-butenyloxy group, a 4-pentenyloxy group, etc.; and a branched alkenyloxy group such as a 2-methyl-2-propenyloxy group, a 2-methyl-2-butenyloxy group, a 3-methyl-2-butenyloxy group, etc.

Of those, as the alkenyloxy group represented by $R^3$, preferred are a vinyloxy group and a 2-propenyloxy group; and more preferred is a 2-propenyloxy group.

In the general formula (I), for the linear or branched alkynyloxy group having from 3 to 8 carbon atoms represented by $R^3$, preferably mentioned are a linear alkynyloxy group such as a 2-propynyloxy group, a 2-butynyloxy group, a 3-butynyloxy group, a 4-pentynyloxy group, a 5-hexynyloxy group, etc.; and a branched alkynyloxy group such as a 1-methyl-2-propynyloxy group, 1-methyl-2-butynyloxy group, 1,1-dimethyl-2-propynyloxy group, etc.

Of those, as the alkynyloxy group represented by $R^3$, preferred is an alkynyloxy group having from 3 to 5 carbon atoms; more preferred are a 2-propynyloxy group, a 3-butynyloxy group, a 1-methyl-2-butynyloxy group, and a 1,1-dimethyl-2-propynyloxy group; even more preferred are a 2-propynyloxy group and a 1,1-dimethyl-2-propynyloxy group.

In the general formula (I), for the aryloxy group having from 6 to 18 carbon atoms represented by $R^3$, preferably mentioned are a phenyloxy group, a tolyloxy group, a xylyloxy group, and a naphthyloxy group.

Of those, as the aryloxy group represented by $R^3$, preferred are a phenyloxy group and a tolyloxy group, and more preferred is a phenyloxy group.

In case where $X^1$ in the general formula (I) is a group —S(=O)$_2$—, the combination of the group $R^1(O)_n$ and the group $R^2$ therein includes the following (a) to (d):
(a) a combination of an alkenyl group (or that is, in the case of n=0) and an alkynyl group,
(b) a combination of an alkenyl group (or that is, in the case of n=0) and an alkynyloxy group,
(c) a combination of an alkenyloxy group (or that is, in the case of n=1) and an alkynyl group,
(d) a combination of an alkenyloxy group (or that is, in the case of n=1) and an alkynyloxy group.

Of those, preferred is the case where the combined substituents (group $R^1(O)n$, group $R^2$) have one oxygen atom, especially the case where $R^2$ is an alkynyloxy group, since the low-temperature and high-temperature cycle properties and the load characteristics after high-temperature charging storage are bettered more.

In case where $X^1$ is a group —P(=O)(—$R^3$)—, preferably, the combined substituents $R^1(O)n$, $R^2$ and $R^3$ have from 1 to 3 oxygen atoms, more preferably 3 oxygen atoms, since the low-temperature and high-temperature cycle properties and the load characteristics after high-temperature charging storage are bettered more.

In case where $X^1$ in the general formula (I) is a group —P(=O)(—$R^3$)—, the combination of the unsaturated bond-having substituents $R^1(O)_n$, $R^2$ and $R^3$ includes the following (x) to (z):
(x) a combination of one carbon-carbon double bond-having group (alkenyl group or alkenyloxy group) and one carbon-carbon triple bond-having group (alkynyl group or alkynyloxy group),
(y) a combination of one carbon-carbon double bond-having group (alkenyl group or alkenyloxy group) and two carbon-carbon triple bond-having groups (alkynyl group or alkynyloxy group),
(z) a combination of two carbon-carbon double bond-having groups (alkenyl group or alkenyloxy group) and one carbon-carbon triple bond-having group (alkynyl group or alkynyloxy group).

Of those, preferred is the combination (x) or (y) and more preferred is the combination (x), since the low-temperature and high-temperature cycle properties and the load characteristics after high-temperature charging storage are bettered more.

The following are preferred examples of the compound represented by the general formula (I).

As the case where $X^1$ is a group —C(=O)—, $R^2$ is an alkynyl group and n is 1, preferably mentioned are alkynoates such as vinyl 3-butynoate, 2-propenyl 3-butynoate, 3-butenyl 3-butynoate, vinyl 4-pentynoate, 2-propenyl 4-pentynoate, 3-butenyl 4-pentynoate, etc.

Of those, preferred are vinyl 3-butynoate and 2-propenyl 3-butynoate; and more preferred is 2-propenyl 3-butynoate.

As the case where $X^1$ is a group —C(=O)—C(=O)—, $R^2$ is an alkynyloxy group and n is 1, preferably mentioned are oxalates such as 2-propynyl vinyl oxalate, 3-butynyl vinyl oxalate, 2-propenyl 2-propynyl oxalate, 3-butynyl 2-propenyl oxalate, 3-butenyl 2-propynyl oxalate, 3-butenyl 3-butynyl oxalate, etc.

Of those, preferred are 2-propynyl vinyl oxalate and 2-propenyl 2-propynyl oxalate; and more preferred is 2-propenyl 2-propynyl oxalate.

As the case where $X^1$ is a group —S(=O)$_2$—, $R^2$ is an alkynyl group and n is 0, preferably mentioned are sulfonyl compounds such as 2-propynyl vinyl sulfone, 2-propenyl 2-propynyl sulfone, 3-butenyl 2-propynyl sulfone, 3-butenyl 2-propynyl sulfone, 1,1-dimethyl-2-propynyl vinyl sulfone, 1,1-dimethyl-2-propynyl 2-propenyl sulfone, etc.

Of those, preferred are 2-propynyl vinyl sulfone and 2-propenyl 2-propynyl sulfone; and more preferred is 2-propenyl 2-propynyl sulfone.

As the case where $X^1$ is a group —S(=O)$_2$—, $R^2$ is an alkynyloxy group and n is 0, preferably mentioned are sulfonates such as 2-propynyl vinylsulfonate, 3-butynyl vinylsulfonate, 1,1-dimethyl-2-propynyl vinylsulfonate, 2-propynyl 2-propene-1-sulfonate, 3-butynyl 2-propene-1-sulfonate, 1-methyl-2-propynyl 2-propene-1-sulfonate, 1,1-dimethyl-2-propynyl 2-propene-1-sulfonate, etc.

Of those, preferred are 2-propynyl vinylsulfonate and 1,1-dimethyl-2-propynyl vinylsulfonate; and more preferred is 2-propynyl vinylsulfonate.

As the case where $X^1$ is a group —S(=O)$_2$—, $R^2$ is an alkynyl group and n is 1, preferably mentioned are sulfonates such as vinyl 2-propyne-1-sulfonate, vinyl 1,1-dimethyl-2-propyne-1-sulfonate, 2-propenyl 2-propyne-1-sulfonate, 2-propenyl 1,1-dimethyl-2-propyne-1-sulfonate, 3-butenyl 2-propyne-1-sulfonate, 3-butenyl 1,1-dimethyl-2-propyne-1-sulfonate, etc.

Of those, preferred are vinyl 2-propyne-1-sulfonate and 2-propenyl 2-propyne-1-sulfonate; and more preferred is 2-propenyl 2-propyne-1-sulfonate.

As the case where $X^1$ is a group —S(=O)$_2$—, $R^2$ is an alkynyloxy group and n is 1, preferably mentioned are sulfates such as 2-propenyl 2-propynylsulfate, 2-propenyl 1,1-dimethyl-2-propynylsulfate, 3-butenyl 2-propynylsulfate, 3-butenyl 1,1-dimethyl-2-propynylsulfate, etc.

Of those, preferred are 2-propenyl 2-propynylsulfate and 2-propenyl 1,1-dimethyl-2-propynylsulfate; and more preferred is 2-propenyl 2-propynylsulfate.

As the case where $X^1$ is a group —P(=O)(—$R^3$)—, $R^2$ is an alkynyl group and n is 0, preferably mentioned are phosphine oxides such as methyl(2-propynyl)(vinyl)phosphine oxide, divinyl(2-propynyl)phosphine oxide, di(2-propynyl)(vinyl)phosphine oxide, di(2-propenyl)(2-propynyl) phosphine oxide, di(2-propynyl)(2-propenyl)phosphine oxide, di(3-butenyl)(2-propynyl)phosphine oxide, di(2-propynyl)(3-butenyl)phosphine oxide, etc.

Of those, preferred are divinyl(2-propynyl)phosphine oxide and di(2-propynyl)(vinyl)phosphine oxide; and more preferred is divinyl(2-propynyl)phosphine oxide.

As the case where $X^1$ is a group —P(=O)(—$R^3$)—, $R^2$ is an alkynyloxy group and n is 0, preferably mentioned are phosphinates such as 2-propynyl methyl(2-propenyl)phosphinate, 2-propynyl 2-butenyl(methyl)phosphinate, 2-propynyl di(2-propenyl)phosphinate, 2-propynyl di(3-butenyl) phosphinate, 1,1-dimethyl-2-propynyl methyl(2-propenyl) phosphinate, 1,1-dimethyl-2-propynyl 2-butenyl(methyl) phosphinate, 1,1-dimethyl-2-propynyl di(2-propenyl) phosphinate, 1,1-dimethyl-2-propynyl di(3-butenyl) phosphinate, etc.

Of those, preferred are 2-propynyl di(2-propenyl)phosphinate and 1,1-dimethyl-2-propynyl di(2-propenyl)phosphinate; and more preferred is 2-propynyl di(2-propenyl) phosphinate.

Also preferably mentioned are phosphonates such as methyl 2-propynyl 2-propenylphosphonate, methyl 2-propynyl 2-butenylphosphonate, 2-propynyl 2-propenyl 2-propenylphosphonate, 3-butenyl 2-propynyl 3-butenylphosphonate, 1,1-dimethyl-2-propynyl methyl 2-propenylphosphonate, 1,1-dimethyl-2-propynyl methyl 2-butenylphosphonate, 1,1-dimethyl-2-propynyl 2-propenyl 2-propenylphosphonate, 3-butenyl 1,1-dimethyl-2-propynyl 3-butenylphosphonate, etc.

Of those, preferred are 2-propynyl 2-propenyl 2-propenylphosphonate and 1,1-dimethyl-2-propynyl 2-propenyl 2-propenylphosphonate; and more preferred is 2-propynyl 2-propenyl 2-propenylphosphonate.

As the case where X' is a group —P(=O)(—$R^3$)—, $R^2$ is an alkynyl group and n is 1, preferably mentioned are phosphinates such as 2-propynyl methyl(2-propynyl)phosphinate, 3-butenyl methyl(2-propynyl)phosphinate, 2-propenyl di(2-propynyl)phosphinate, 3-butenyl di(2-propynyl) phosphinate, 2-propenyl 2-propynyl(2-propenyl) phosphinate, 3-butenyl 2-propynyl(2-propenyl)phosphinate, etc.

Of those, preferred are 2-propenyl di(2-propynyl)phosphinate and 2-propenyl 2-propynyl(2-propenyl)phosphonate; and more preferred is 2-propenyl 2-propynyl(2-propenyl)phosphinate.

Also preferably mentioned are phosphonates such as 2-propynyl 2-propenyl methylphosphonate, 3-butenyl 2-propynyl methylphosphonate, 1,1-dimethyl-2-propynyl 2-propenyl methylphosphonate, 3-butenyl 1,1-dimethyl-2-propynyl methylphosphonate, 2-propynyl 2-propenyl ethylphosphonate, 3-butenyl 2-propynyl ethylphosphonate, 1,1-dimethyl-2-propynyl 2-propenyl ethylphosphonate, 3-butenyl 1,1-dimethyl-2-propynyl ethylphosphonate, etc.

Of those, preferred are 2-propynyl 2-propenyl methylphosphonate and 2-propynyl 2-propenyl ethylphosphonate; and more preferred is 2-propynyl 2-propenyl methylphosphonate.

As the case where X' is a group —P(=O)(—$R^3$)—, $R^2$ is an alkynyloxy group and n is 1, preferably mentioned are phosphates such as methyl 2-propenyl 2-propynyl phosphate, ethyl 2-propenyl 2-propynyl phosphate, 2-butenyl methyl 2-propynyl phosphate, 2-butenyl ethyl 2-propynyl phosphate, 1,1-dimethyl-2-propynyl methyl 2-propenyl phosphate, 1,1-dimethyl-2-propynyl ethyl 2-propenyl phosphate, 2-butenyl 1,1-dimethyl-2-propynyl methyl phosphate, 2-butenyl ethyl 1,1-dimethyl-2-propynyl phosphate, etc.

Of those, preferred are methyl 2-propenyl 2-propynyl phosphate and ethyl 2-propenyl 2-propynyl phosphate; and more preferred is ethyl 2-propenyl 2-propynyl phosphate.

From the viewpoint of improving the low-temperature and high-temperature cycle properties and improving the load characteristics after high-temperature charging storage, preferred are the compounds represented by the above-mentioned general formula (I) where $X^1$ is a group —C(=O)—, a group —C(=O)—C(=O)— or a group —S(=O)$_2$—, more preferably a group —C(=O)—C(=O)— or a group —S(=O)$_2$—, even more preferably a group —S(=O)$_2$—. Of those, preferred are 2-propenyl 3-butynoate, 2-propenyl 2-propynyl oxalate, 2-propynyl vinylsulfonate, 1,1-dimethyl-2-propynyl vinylsulfonate, vinyl 2-propyne-1-sulfonate, and 2-propenyl 2-propyne-1-sulfonate; and more preferred are 2-propenyl 2-propynyl oxalate, 2-propynyl vinylsulfonate, and 2-propenyl 2-propyne-1-sulfonate; and even more preferred is 2-propynyl vinylsulfonate.

In the nonaqueous electrolytic solution of the present invention, the content of at least one alkynyl compound represented by the general formula (I) is from 0.01 to 10% by mass of the nonaqueous electrolytic solution. When the content is more than 10% by mass, then a surface film may be formed excessively on an electrode to worsen low-temperature cycle properties; but when less than 0.01% by mass, then the surface film formation would be insufficient, therefore failing in attaining the effect of improving high-temperature cycle properties. The content is preferably at least 0.05% by mass in the nonaqueous electrolytic solution, more preferably at least 0.1% by mass, even more preferably at least 0.3% by mass; and its upper limit is preferably at most 7% by mass, more preferably at most 5% by mass, even more preferably at most 3% by mass.

Even when used alone, the compound represented by the general formula (I) can improve the low-temperature and high-temperature cycle properties and the load characteristics after high-temperature charging storage, but when combined with a nonaqueous solvent and an electrolyte salt to be mentioned below, the compound can exhibit a specific effect of synergistically improving the low-temperature and high-temperature cycle properties and the load characteristics after high-temperature charging storage. Though the reason is not clear, it may be considered that a mixture surface film having a high ionic conductivity and comprising the alkynyl compound represented by the general formula (I) and, as combined, those constitutive elements of the nonaqueous solvent and the electrolyte salt could be formed.

(Alkynyl Sulfonate Compound Represented by General Formula (III))

[Chemical Formula 8]

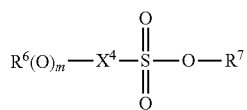

(III)

In the general formula (III), $R^7$ represents an linear or branched alkynyl group having from 3 to 8 carbon atoms; $X^4$ represents an alkylene group having from 1 to 8 carbon atoms, or a divalent linking group having from 2 to 8 carbon atoms and containing at least one ether bond; m indicates 0 or 1.

When m is 0, $R^6$ represents a formyl group, a linear or branched acyl group having from 2 to 8 carbon atoms, an arylcarbonyl group having from 7 to 15 carbon atoms, a linear or branched alkanesulfonyl group having from 1 to 8 carbon atoms, an linear or branched alkynyloxysulfonyl group having from 3 to 8 carbon atoms, an arylsulfonyl group having from 6 to 15 carbon atoms, a linear or branched dialkylphosphoryl group having from 2 to 16 carbon atoms, a linear or branched alkyl(alkoxy)phosphoryl group having from 2 to 16 carbon atoms, or a linear or branched dialkylphosphoryl group having from 2 to 16 carbon atoms.

When m is 1, $R^6$ represents a formyl group, a linear or branched alkyl group having from 1 to 8 carbon atoms, a linear or branched acyl group having from 2 to 8 carbon atoms, an arylcarbonyl group having from 7 to 15 carbon atoms, a linear or branched alkanesulfonyl group having from 1 to 8 carbon atoms, an arylsulfonyl group having from 6 to 15 carbon atoms, a linear or branched dialkylphosphoryl group having from 2 to 16 carbon atoms, a linear or branched alkyl(alkoxy)phosphoryl group having from 2 to 16 carbon atoms, or a linear or branched dialkoxyphosphoryl group having from 2 to 16 carbon atoms. At least one hydrogen atom on the carbon atom of $R^7$, $X^4$ and $R^6$ may be substituted with a halogen atom.

In the general formula (III), the alkynyl group represented by $R^7$ is preferably a linear alkynyl group such as a 2-propynyl group, a 2-butynyl group, a 3-butynyl group, a 4-pentynyl group, a 5-hexynyl group, etc.; or a branched alkynyl group such as a 1-methyl-2-propynyl group, a 1-methyl-2-butynyl group, a 1,1-dimethyl-2-propynyl group, etc.

Of those, the alkynyl group represented by $R^7$ is more preferably a 2-propynyl group, a 2-butynyl group, a 3-butynyl group, a 1-methyl-2-propynyl group or a 1,1-dimethyl-2-propynyl group, further preferably a 2-propynyl group, a 3-butynyl group or a 1,1-dimethyl-2-propynyl group, and most preferably a 2-propynyl group.

In the general formula (III), the linear or branched alkylene group having from 1 to 8 carbon atoms of $X^4$ includes an unsubstituted alkylene group such as a methylene group, an ethylene group, a trimethylene group, a tetramethylene group, a pentamethylene group, a hexamethylene group, etc.; and a substituted alkylene group such as an ethylidene group, a propane-1,2-diyl group, a propylidene group, an isopropylidene group, a butane-1,3-diyl group, 2-methylpropane-1,2-diyl group, a butylidene group, etc. Of those, preferred is an alkylene group having from 1 to 4 carbon atoms, more preferred is an alkylene group having from 1 to 3 carbon atoms, even more preferred is an alkylene group having 2 or 3 carbon atoms, and especially preferred is an alkylene group having 2 carbon atoms. Concretely, preferred are an unsubstituted alkylene group such as a methylene group, an ethylene group, a trimethylene group, a tetramethylene group, a pentamethylene group, etc.; and a substituted alkylene group such as an ethylidene group, a propane-1,2-diyl group, a propylidene group, an isopropylidene group, etc.; more preferred are a methylene group, an ethylene group, a trimethylene group, an ethylidene group, a propane-1,2-diyl group, a propylidene group, and an isopropylidene group; even more preferred are an ethylene group, an ethylidene group, and a trimethylene group; and especially preferred is an ethylene group.

The divalent linking group having from 2 to 8 carbon atoms and containing at least one ether bond is preferably —CH$_2$OCH$_2$—C$_2$H$_4$OC$_2$H$_4$— or —C$_2$H$_4$OC$_2$H$_4$OC$_2$H$_4$—, more preferably —C$_2$H$_4$OC$_2$H$_4$—. The number of the ether bond is from 1 to 3, but is preferably 1. The carbon number of the two alkylene groups at both sides of the ether oxygen may be asymmetric or symmetric, but is preferably symmetric. The alkylene groups at both sides of the ether oxygen may be branched.

In the general formula (III), m is 0 or 1, but more preferably m is 1.

When m is 0, $R^6$ is more preferably a formyl group, a linear or branched acyl group having from 2 to 8 carbon atoms, an arylcarbonyl group having from 7 to 15 carbon atoms, a linear or branched alkanesulfonyl group having from 1 to 8 carbon atoms, an linear or branched alkynyloxysulfonyl group having from 3 to 8 carbon atoms, or an arylsulfonyl group having from 6 to 15 carbon atoms, even more preferably a linear or branched acyl group having from 2 to 8 carbon atoms, or a linear or branched alkynyloxysulfonyl group having from 3 to 8 carbon atoms, especially preferably a linear or branched alkynyloxysulfonyl group having from 3 to 8 carbon atoms.

When m is 1, $R^6$ is more preferably a formyl group, a linear or branched alkyl group having from 1 to 8 carbon atoms, a linear or branched acyl group having from 2 to 8 carbon atoms, an arylcarbonyl group having from 7 to 15 carbon atoms, a linear or branched alkanesulfonyl group having from 1 to 8 carbon atoms, or an arylsulfonyl group having from 6 to 15 carbon atoms, even more preferably a linear or branched acyl group having from 2 to 8 carbon atoms, or a linear or branched alkanesulfonyl group having from 1 to 8 carbon atoms.

The linear acyl group having from 2 to 8 carbon atoms represented by $R^6$ is preferably an acetyl group, a propionyl group, a butyryl group, an isobutyryl group, or a pivaloyl group, more preferably acetyl group or a propionyl group, even more preferably an acetyl group.

The arylcarbonyl group having from 7 to 15 carbon atoms represented by $R^6$ is preferably a benzoyl group, a toluoylcarbonyl group, or a naphthoyl group, more preferably a benzoyl group.

The linear or branched alkanesulfonyl group having from 1 to 8 carbon atoms represented by $R^6$ is preferably a linear alkanesulfonyl group such as a methanesulfonyl group, an ethanesulfonyl group, a propanesulfonyl group, a butanesulfonyl group, a pentanesulfonyl group, a hexanesulfonyl group, a heptanesulfonyl group, an octanesulfonyl group, etc.; a branched alkanesulfonyl group such as a 2-propanesulfonyl group, a 2-butanesulfonyl group, a t-butanesulfonyl group, etc.; or a haloalkanesulfonyl group such as a fluoromethanesulfonyl group, a trifluoromethanesulfonyl group, a trifluoroethanesulfonyl group, a pentafluoropropanesulfonyl group, etc. Of those, more preferred are a linear alkanesulfonyl group and a haloalkanesulfonyl group; even more preferred are a methanesulfonyl group, an ethanesulfonyl group, and a trifluoromethanesulfonyl group; and especially preferred is a methanesulfonyl group.

The linear or branched alkynyloxysulfonyl group having from 3 to 8 carbon atoms represented by $R^6$ is preferably a 2-propynyloxysulfonyl group, a 2-butynyloxysulfonyl group, a 3-butynyloxysulfonyl group, a 4-pentynyloxysulfonyl group, a 5-hexynyloxysulfonyl group, a 1-methyl-2-propynyloxysulfonyl group, a 1-methyl-2-butynyloxysulfonyl group, or a 1,1-dimethyl-2-propynyloxysulfonyl group, more preferably a 2-propynyloxysulfonyl group, or a 1-methyl-2-propynyloxysulfonyl group, even more preferably a 2-propynyloxysulfonyl group.

The arylsulfonyl group having from 6 to 15 carbon atoms represented by $R^6$ is preferably a benzenesulfonyl group, a toluenesulfonyl group, a 1-naphthalenesulfonyl group, or a 2-naphthalenesulfonyl group, more preferably a benzenesulfonyl group or a toluenesulfonyl group.

The linear or branched dialkylphosphonyl group having from 2 to 16 carbon atoms represented by $R^6$ is preferably a dimethylphosphonyl group, a diethylphosphonyl group, a dipropylphosphonyl group, or a dibutylphosphonyl group, more preferably a dimethylphosphonyl group or a diethylphosphonyl group.

The linear or branched alkyl(alkoxy)phosphoryl group having from 2 to 16 carbon atoms represented by $R^6$ is preferably a methyl(methoxyl)phosphoryl group, an ethyl(ethoxyl)phosphoryl group, a propyl(propyloxyl)phosphoryl group, or a butyl(butoxyl)phosphoryl group, more preferably a methyl(methoxyl)phosphoryl group or an ethyl(ethoxyl)phosphoryl group.

The linear or branched dialkoxyphosphoryl group having from 2 to 16 carbon atoms represented by $R^6$ is preferably a dimethoxyphosphoryl group, a diethoxyphosphoryl group, a dipropoxyphosphoryl group, or a dibutoxyphosphoryl group, more preferably a dimethoxyphosphoryl group or diethoxyphosphoryl group.

In case where the substituents $R^7$, $R^6$ and $X^2$ are the above-mentioned preferred substituents, the embodiment is preferred since the low-temperature and high-temperature cycle properties and the load characteristics after high-temperature charging storage are markedly improved.

The following are preferred examples of the alkynyl sulfonate compound represented by the above-mentioned general formula (III) where $R^7$ is a 2-propynyl group.

(A-1) As the case where m is 0 and $R^6$ is a formyl group, preferably mentioned are 2-propynyl 2-oxoethanesulfonate, 2-propynyl 3-oxopropanesulfonate, 2-propynyl 4-oxobutanesulfonate, 2-propynyl 5-oxopentanesulfonate, 2-propynyl 6-oxohexanesulfonate, 2-propynyl 7-oxoheptanesulfonate, 2-propynyl 3-oxopropoxymethanesulfonate, etc.

(A-2) As the case where m is 0 and $R^6$ is an acyl group, preferably mentioned are 2-propynyl 2-oxopropanesulfonate, 2-propynyl 3-oxobutanesulfonate, 2-propynyl 4-oxopentanesulfonate, 2-propynyl 5-oxohexanesulfonate, 2-propynyl 6-oxoheptanesulfonate, 2-propynyl 7-oxooctanesulfonate, 2-propynyl 2-oxobutanesulfonate, 2-propynyl 3-oxopentanesulfonate, 2-propynyl 4-oxohexanesulfonate, 2-propynyl 5-oxohepetanesulfonate, 2-propynyl 6-oxooctanesulfonate, 2-propynyl 7-oxononanesulfonate, 2-propynyl 2-(3-oxobutoxy)ethanesulfonate, etc.

(A-3) As the case where m is 0 and $R^6$ is a sulfonyl group, preferably mentioned are the following compounds (A-3-1), (A-3-2), (A-3-3), (A-3-4), (A-3-5), etc.

(A-3-1): 2-Propynyl methanesulfonylmethanesulfonate 2-propynyl 2-(methanesulfonyl)ethanesulfonate, 2-propynyl 3-(methanesulfonyl)propanesulfonate, 2-propynyl 4-(methanesulfonyl)butanesulfonate, 2-propynyl 5-(methanesulfonyl)pentanesulfonate, 2-propynyl 6-(methanesulfonyl)hexanesulfonate, 2-propynyl ethanesulfonylmethanesulfonate, 2-propynyl 2-(ethanesulfonyl)ethanesulfonate, 2-propynyl 3-(ethanesulfonyl)propanesulfonate, 2-propynyl 4-(ethanesulfonyl)butanesulfonate, 2-propynyl 5-(ethanesulfonyl)pentanesulfonate, 2-propynyl 6-(ethanesulfonyl)hexanesulfonate, 2-propynyl trifluoromethanesulfonylmethanesulfonate, 2-propynyl 2-(trifluoromethanesulfonyl)ethanesulfonate, 2-propynyl 3-(trifluoromethanesulfonyl)propanesulfonate, 2-propynyl 4-(trifluoromethanesulfonyl)butanesulfonate, 2-propynyl 5-(trifluoromethanesulfonyl)pentanesulfonate, 2-propynyl 6-(trifluoromethanesulfonyl)hexanesulfonate, 2-propynyl 2-(2-(methanesulfonyl)ethoxy)ethanesulfonate.

(A-3-2): 2-propynyl benzenesulfonylmethanesulfonate, 2-propynyl 2-(benzenesulfonyl)ethanesulfonate, 2-propynyl 3-(benzenesulfonyl)propanesulfonate, 2-propynyl 4-(benzenesulfonyl)butanesulfonate, 2-propynyl 5-(benzenesulfonyl)pentanesulfonate, 2-propynyl 6-(benzenesulfonyl)hexanesulfonate, 2-propynyl 4-methylbenzenesulfonylmethanesulfonate, 2-propynyl 2-(4-methylbenzenesulfonyl)ethanesulfonate, 2-propynyl 3-(4-methylbenzenesulfonyl)propanesulfonate, 2-propynyl 4-(4-methylbenzenesulfonyl)butanesulfonate, 2-propynyl 5-(4-methylbenzenesulfonyl)pentanesulfonate, 2-propynyl 6-(4-methylbenzenesulfonyl)hexanesulfonate, 2-propynyl 4-fluorobenzenesulfonylmethanesulfonate, 2-propynyl 2-(4-fluorobenzenesulfonyl)ethanesulfonate, 2-propynyl 3-(4-fluorobenzenesulfonyl)propanesulfonate, 2-propynyl 4-(4-fluorobenzenesulfonyl)butanesulfonate, 2-propynyl 5-(4-fluorobenzenesulfonyl)pentanesulfonate, 2-propynyl 6-(4-fluorobenzenesulfonyl)hexanesulfonate, 2-propynyl 2-(2-benzenesulfonylethoxy)ethanesulfonate.

(A-3-3): 2-Propynyl methoxysulfonylmethanesulfonate, 2-propynyl 2-(methoxysulfonyl)ethanesulfonate, 2-propynyl 3-(methoxysulfonyl)propanesulfonate, 2-propynyl 4-(methoxysulfonyl)butanesulfonate, 2-propynyl 5-(methoxysulfonyl)pentanesulfonate, 2-propynyl 6-(methoxysulfonyl)hexanesulfonate, 2-propynyl ethoxysulfonylmethanesulfonate, 2-propynyl 2-(ethoxysulfonyl)ethanesulfonate, 2-propynyl 3-(ethoxysulfonyl)propanesulfonate, 2-propynyl 4-(ethoxysulfonyl)butanesulfonate, 2-propynyl 5-(ethoxysulfonyl)pentanesulfonate, 2-propynyl 6-(ethoxysulfonyl)hexanesulfonate, 2-propynyl 2-(2-(methoxysulfonyl)ethoxy)ethanesulfonate.

(A-3-4): 2-Propynyl 2-propenyloxysulfonylmethanesulfonate, 2-propynyl 2-(2-propenyloxysulfonyl)ethanesulfonate, 2-propynyl 3-(2-(propenyloxysulfonyl)propanesulfonate, 2-propynyl 4-(2-propenyloxysulfonyl)butanesulfonate, 2-propynyl 5-(2-propenyloxysulfonyl)pentanesulfonate, 2-propynyl 6-(2-propenyloxysulfonyl)hexanesulfonate, 2-propynyl 2-(2-(2-propenyloxysulfonyl)ethoxy)ethanesulfonate.

(A-3-5): Di(2-propynyl)methane-1,1-disulfonate, di(2-propynyl)ethane-1,2-disulfonate, di(2-propynyl)propane-1,3-disulfonate, di(2-propynyl)butane-1,4-disulfonate, di(2-propynyl)pentane-1,5-disulfonate, di(2-propynyl)hexane-1,6-disulfonate, di(2-propynyl)2,2'-oxydiethanesulfonate.

(A-4) As the case where m is 0 and $R^6$ is a phosphoryl group, preferably mentioned are the following compounds (A-4-1), (A-4-2), (A-4-3), etc.

(A-4-1) 2-Propynyl dimethoxyphosphorylmethanesulfonate, 2-propynyl 2-(dimethoxyphosphoryl)ethanesulfonate, 2-propynyl 3-(dimethoxyphosphoryl)propanesulfonate, 2-propynyl 4-(dimethoxyphosphoryl)butanesulfonate, 2-propynyl 5-(dimethoxyphosphoryl)pentanesulfonate, 2-propynyl 6-(dimethoxyphosphoryl)hexanesulfonate, 2-propynyl diethoxyphosphorylmethanesulfonate, 2-propynyl 2-(diethoxyphosphoryl)ethanesulfonate, 2-propynyl 3-(diethoxyphosphoryl)propanesulfonate, 2-propynyl 4-(diethoxyphosphoryl)butanesulfonate, 2-propynyl 5-(diethoxyphosphoryl)pentanesulfonate, 2-propynyl 6-(diethoxyphosphoryl)hexanesulfonate, 2-propynyl 2-(2-(dimethoxyphosphoryl)ethoxy)ethanesulfonate.

(A-4-2): 2-Propynyl methoxy(methyl)phosphorylmethanesulfonate, 2-propynyl 2-(methoxy(methyl)phosphoryl)ethanesulfonate, 2-propynyl 3-(methoxy(methyl)phosphoryl)propanesulfonate, 2-propynyl 4-(methoxy(methyl)phosphoryl)butanesulfonate, 2-propynyl 5-(methoxy(methyl)phosphoryl)pentanesulfonate, 2-propynyl 6-(methoxy(methyl)phosphoryl)hexanesulfonate, 2-propynyl 2-(2-methoxy(methyl)phosphoryl)ethoxy)ethanesulfonate, 2-propynyl ethoxy(methyl)phosphorylmethanesulfonate, 2-propynyl 2-(ethoxy(methyl)phosphoryl)ethanesulfonate, 2-propynyl 3-(ethoxy(methyl)phosphoryl)propanesulfonate, 2-propynyl ethyl(methoxy)phosphorylmethanesulfonate, 2-propynyl 2-(ethyl(methoxy)phosphoryl)ethanesulfonate, 2-propynyl 3-(ethyl(methoxy)phosphoryl)propanesulfonate.

(A-4-3): 2-Propynyl dimethylphosphorylmethanesulfonate, 2-propynyl 2-(dimethylphosphoryl)ethanesulfonate, 2-propynyl 3-(dimethylphosphoryl)propanesulfonate, 2-propynyl 4-(dimethylphosphoryl)butanesulfonate, 2-propynyl 5-(dimethylphosphoryl)pentanesulfonate, 2-propynyl 6-(dimethylphosphoryl)hexanesulfonate, 2-propynyl 2-(2-(dimethylphosphoryl)ethoxy)ethanesulfonate.

(B-1) As the case where m is 1 and $R^6$ is an alkyl group, preferably mentioned are 2-propynyl methoxymethanesulfonate, 2-propynyl 2-methoxyethanesulfonate, 2-propynyl 3-methoxypropanesulfonate, 2-propynyl 4-methoxybutanesulfonate, 2-propynyl 5-methoxypentanesulfonate, 2-propynyl 6-methoxyhexanesulfonate, 2-propynyl ethoxymethanesulfonate, 2-propynyl 2-ethoxyethanesulfonate, 2-propynyl 3-ethoxypropanesulfonate, 2-propynyl 4-ethoxybutanesulfonate, 2-propynyl 5-ethoxypentanesulfonate, 2-propynyl 6-ethoxyhexanesulfonate, 2-propynyl 2-(2-methoxyethoxy)ethanesulfonate, etc.

(B-2) As the case where m is 1 and $R^6$ is a formyl group, preferably mentioned are 2-propynyl formyloxymethanesulfonate, 2-propynyl 2-(formyloxy)ethanesulfonate, 2-propynyl 3-(formyloxy)propanesulfonate, 2-propynyl 4-(formyloxy)butanesulfonate, 2-propynyl 5-(formyloxy)pentanesulfonate, 2-propynyl 6-(formyloxy)hexanesulfonate, 2-propynyl 2-(2-(formyloxy)ethoxy)ethanesulfonate, etc.

(B-3) As the case where m is 1 and $R^6$ is an acyl group, preferably mentioned are 2-propynyl acetyloxymethanesulfonate, 2-propynyl 2-(acetyloxy)ethanesulfonate, 2-propynyl 3-(acetyloxy)propanesulfonate, 2-propynyl 4-(acetyloxy)butanesulfonate, 2-propynyl 5-(acetyloxy)pentanesulfonate, 2-propynyl 6-(acetyloxy)hexanesulfonate, 2-propynyl propionyloxymethanesulfonate, 2-propynyl 2-(propionyloxy)ethanesulfonate, 2-propynyl 3-(propionyloxy)propanesulfonate, 2-propynyl 4-(propionyloxy)butanesulfonate, 2-propynyl 5-(propionyloxy)pentanesulfonate, 2-propynyl 6-(propionyloxy)hexanesulfonate, 2-propynyl 2-(2-(acetyloxy)ethoxy)ethanesulfonate, etc.

(B-4) As the case where m is 1 and $R^6$ is a sulfonyl group, preferably mentioned are 2-propynyl methanesulfonyloxymethanesulfonate, 2-propynyl 2-(methanesulfonyloxy)ethanesulfonate, 2-propynyl 3-(methanesulfonyloxy)propanesulfonate, 2-propynyl 4-(methanesulfonyloxy)butanesulfonate, 2-propynyl 5-(methanesulfonyloxy)pentanesulfonate, 2-propynyl 6-(methanesulfonyloxy)hexanesulfonate, 2-propynyl ethanesulfonyloxymethanesulfonate, 2-propynyl 2-(ethanesulfonyloxy)ethanesulfonate, 2-propynyl 3-(ethanesulfonyloxy)propanesulfonate, 2-propynyl 4-(ethanesulfonyloxy)butanesulfonate, 2-propynyl 5-(ethanesulfonyloxy)pentanesulfonate, 2-propynyl 5-(ethanesulfonyloxy)hexanesulfonate, 2-propynyl trifluoromethanesulfonyloxymethanesulfonate, 2-propynyl 2-(trifluoromethanesulfonyloxy)ethanesulfonate, 2-propynyl 3-(trifluoromethanesulfonyloxy)propanesulfonate, 2-propynyl 4-(trifluoromethanesulfonyloxy)butanesulfonate, 2-propynyl 5-(trifluoromethanesulfonyloxy)pentanesulfonate, 2-propynyl 6-(trifluoromethanesulfonyloxy)hexanesulfonate, 2-propynyl 2-(2-(methanesulfonyloxy)ethoxy)ethanesulfonate, etc.

(B-5) As the case where m is 1 and $R^6$ is a phosphoryl group, preferably mentioned are the following compounds (B-5-1), (B-5-2), (B-5-3), etc.

(B-5-1) 2-Propynyl dimethoxyphosphoryloxymethanesulfonate, 2-propynyl 2-(dimethoxyphosphoryloxy)ethanesulfonate, 2-propynyl 3-(dimethoxyphosphoryloxy)propanesulfonate, 2-propynyl 4-(dimethoxyphosphoryloxy)butanesulfonate, 2-propynyl 5-(dimethoxyphosphoryloxy)pentanesulfonate, 2-propynyl 6-(dimethoxyphosphoryloxy)hexanesulfonate, 2-propynyl diethoxyphosphoryloxymethanesulfonate, 2-propynyl 2-(diethoxyphosphoryloxy)ethanesulfonate, 2-propynyl 3-(diethoxyphosphoryloxy)propanesulfonate, 2-propynyl 4-(diethoxyphosphoryloxy)butanesulfonate, 2-propynyl 5-(diethoxyphosphoryloxy)pentanesulfonate, 2-propynyl 6-(diethoxyphosphoryloxy)hexanesulfonate, 2-propynyl 2-(2-(dimethoxyphosphoryloxy)ethoxy)ethanesulfonate.

(B-5-2) 2-Propynyl methoxy(methyl)phosphoryloxymethanesulfonate, 2-propynyl 2-(methoxy)methyl)phosphoryloxy)ethanesulfonate, 2-propynyl 3-(methoxy(methyl)phosphoryloxy)propanesulfonate, 2-propynyl 4-(methoxy(methyl)phosphoryloxy)butanesulfonate, 2-propynyl 5-(methoxy(methyl)phosphoryloxy)pentanesulfonate, 2-propynyl 6-(methoxy(methyl)phosphoryloxy)hexanesulfonate, 2-propynyl 2-(2-(methoxy(methyl)phosphoryloxy)ethoxy)ethanesulfonate, 2-propynyl ethoxy(methyl)phosphoryloxymethanesulfonate, 2-propynyl 2-(ethoxy(methyl)phosphoryloxy)ethanesulfonate, 2-propynyl 3-(ethoxy(methyl)phosphoryloxy)propanesulfonate, 2-propynyl ethyl(methoxy)phosphoryloxymethanesulfonate, 2-propynyl 2-(ethyl(methoxy)phosphoryloxy)ethanesulfonate, 2-propynyl 3-(ethyl(methoxy)phosphoryloxy)propanesulfonate.

(B-5-3) 2-Propynyl dimethylphosphoryloxymethanesulfonate, 2-propynyl 2-(dimethylphosphoryloxy)ethanesulfonate, 2-propynyl 3-(dimethylphosphoryloxy)propanesulfonate, 2-propynyl 4-(dimethylphosphoryloxy)butanesulfonate, 2-propynyl 5-(dimethylphosphoryloxy)pentanesulfonate, 2-propynyl 6-(dimethylphosphoryloxy)hexanesulfonate, 2-propynyl 2-(2-(dimethylphosphoryloxy)ethoxy)ethanesulfonate.

From the viewpoint of improving the load characteristics after high-temperature charging storage, the following are preferred from among the alkynyl sulfonate compounds represented by the general formula (III). (A-1): 2-Propynyl 2-oxoethanesulfonate, 2-propynyl 3-oxopropanesulfonate, 2-propynyl 4-oxobutanesulfonate; (A-2): 2-propynyl 2-oxopropanesulfonate, 2-propynyl 3-oxobutanesulfonate, 2-propynyl 4-oxopentanesulfonate, 2-propynyl 5-oxohexanesulfonate; (A-3-1): 2-propynyl methanesulfonylmethanesulfonate, 2-propynyl 2-(methanesulfonyl)ethanesulfonate, 2-propynyl 3-(methanesulfonyl)propanesulfonate; (A-3-3): 2-propynyl methoxysulfonylmethanesulfonate, 2-propynyl 2-(methoxysulfonyl)ethanesulfonate, 2-propynyl 3-(methoxysulfonyl)propanesulfonate; (A-3-4): 2-propynyl 2-propenyloxysulfonylmethanesulfonate, 2-propynyl 2-(2-propenyloxysulfonyl)ethanesulfonate, 2-propynyl 3-(2-propenyloxysulfonyl)propanesulfonate; (A-3-5): di(2-propynyl)methane-1,1-disulfonate, di(2-propynyl)ethane-1,2-disulfonate, di(2-propynyl)propane-1,3-disulfonate, di(2-propynyl)2,2'-oxydiethanesulfonate; (B-1): 2-propynyl methoxymethanesulfonate, 2-propynyl 2-methoxyethanesulfonate, 2-propynyl 3-methoxypropanesulfonate; (B-2): 2-propynyl formyloxymethanesulfonate, 2-propynyl 2-(formyloxy)ethanesulfonate, 2-propynyl 3-(formyloxy)propanesulfonate; (B-3): 2-propynyl acetyloxymethanesulfonate, 2-propynyl 2-(acetyloxy)ethanesulfonate, 2-propynyl 3-(acetyloxy)propanesulfonate; (B-4): 2-propynyl methanesulfonyloxymethanesulfonate, 2-propynyl 2-(methanesulfonyloxy)ethanesulfonate, 2-propynyl 3-(methanesulfonyloxy)propanesulfonate; (B-5) 2-propynyl dimethoxyphosphoryloxymethanesulfonate, 2-propynyl 2-(dimethoxyphosphoryloxy)ethanesulfonate, 2-propynyl 3-(dimethoxyphosphoryloxy)propane sulfonate.

Of the alkynyl sulfonate compounds represented by the general formula (III), more preferred are (A-3-5) di(2-propynyl)ethane-1,2-disulfonate, di(2-propynyl)propane-1,3-disulfonate, di(2-propynyl)2,2'-oxydiethanesulfonate; (B-1) 2-propynyl 2-methoxyethanesulfonate, 2-propynyl 3-methoxypropanesulfonate; (B-2) 2-propynyl 2-(formyloxy)ethanesulfonate, 2-propynyl 3-(formyloxy)propanesulfonate; (B-3) 2-propynyl 2-(acetyloxy)ethanesulfonate, 2-propynyl 3-(acetyloxy)propanesulfonate; (B-4) 2-propynyl 2-(methanesulfonyloxy)ethanesulfonate, 2-propynyl 3-(methanesulfonyloxy)propanesulfonate; and even more preferred are (A-3-5) di(2-propynyl)ethane-1,2-disulfonate, di(2-propynyl)propane-1,3-disulfonate; (B-1) 2-propynyl 2-methoxyethanesulfonate; (B-3) 2-propynyl 2-(acetyloxy)ethanesulfonate, 2-propynyl 3-(acetyloxy)propanesulfonate; (B-4) 2-propynyl 2-(methanesulfonyloxy)ethanesulfonate, 2-propynyl 3-(methanesulfonyloxy)propanesulfonate.

In the nonaqueous electrolytic solution of the present invention, the content of at least one alkynyl sulfonate compound represented by the general formula (III) is from 0.01 to 10% by mass of the nonaqueous electrolytic solution. When the content is more than 10% by mass, then a surface film may be formed excessively on an electrode to worsen low-temperature and high-temperature cycle properties and load characteristics after high-temperature charging storage; but when less than 0.01% by mass, then the surface film formation would be insufficient, therefore failing in attaining the effect of improving low-temperature and high-temperature cycle properties and load characteristics after high-temperature charging storage. The content is preferably at least 0.1% by mass in the nonaqueous electrolytic solution, more preferably at least 0.5% by mass, even more preferably at least 1% by mass; and its upper limit is preferably at most 7% by mass, more preferably at most 5% by mass, even more preferably at most 3% by mass.

Even when used alone, the alkynyl sulfonate compound represented by the general formula (III) can improve the low-temperature and high-temperature cycle properties and the load characteristics after high-temperature charging storage, but when combined with a nonaqueous solvent, an electrolyte salt and other additives to be mentioned below, the compound can exhibit a specific effect of synergistically improving the low-temperature and high-temperature cycle properties and the load characteristics after high-temperature charging storage. Though the reason is not clear, it may be considered that a mixture surface film having a high ionic conductivity and comprising the alkynyl sulfonate compound represented by the general formula (III) and, as combined, those constitutive elements of the nonaqueous solvent, the electrolyte salt and the other additives could be formed.

[Nonaqueous Solvent]

The nonaqueous solvent for use in the nonaqueous electrolytic solution of the present invention includes cyclic carbonates, linear carbonates, linear esters, lactones, ethers, amides, phosphates, sulfones, nitriles, S=O bond-containing compounds (excluding alkynyl sulfonate compounds represented by the general formula (III)), etc.

(Cyclic Carbonates)

The cyclic carbonates include ethylene carbonate (EC), propylene carbonate (PC), butylene carbonate (BC), 4-fluoro-1,3-dioxolan-2-one (FEC), trans or cis-4,5-difluoro-1,3-dioxolan-2-one (hereinafter the two are collectively called "DFEC"), vinylene carbonate (VC), vinylethylene carbonate (VEC), etc. Of those, preferred is use of at least one cyclic carbonate having a carbon-carbon double bond or a fluorine atom, as markedly enhancing the effect of improving high-temperature cycle properties and load characteristics after high-temperature charging storage; and more preferred is use of both a cyclic carbonate having a carbon-carbon double bond and a cyclic carbonate having a fluorine atom. As the cyclic carbonate having a carbon-carbon double bond, more preferred are VC and VEC; and as the cyclic carbonate having a fluorine atom, more preferred are FEC and DFEC.

The content of the fluorine atom-containing cyclic carbonate is preferably at least 0.07% by volume relative to the total volume of the nonaqueous solvent, more preferably at least 4% by volume, even more preferably at least 7% by volume, from the viewpoint of improving the low-temperature and high-temperature cycle properties and the load characteristics after high-temperature charging storage; and the upper limit thereof is preferably at most 35% by volume, more preferably at most 25% by volume, even more preferably at most 15% by volume. Also from the same viewpoint as above, the solvent preferably contain PC. The PC content is preferably at least 0.03% by volume relative to the total volume of the nonaqueous solvent, more preferably at least 1% by volume, even more preferably at least 3% by volume; and the upper limit thereof is preferably at most 25% by volume, more preferably at most 15% by volume, even more preferably at most 10% by volume.

One kind of those solvents may be used, but using two or more different kinds as combined is preferred as further enhancing the effect of improving the above-mentioned battery performance. Even more preferably, three or more different kinds are combined.

Preferred combinations of the cyclic carbonates include EC and VC; PC and VC; FEC and VC; FEC and EC; FEC and PC; DFEC and EC; DFEC and PC; DFEC and VC; DFEC and VEC; EC and PC and VC; EC and FEC and VC; EC and VC and VEC; FEC and PC and VC; DFEC and PC and VC; DFEC and EC and VC; FEC and EC and PC and VC; DFEC and EC and PC and VC, etc. Of those combinations, more preferred combinations are EC and VC; FEC and EC; DFEC and PC; FEC and EC and PC; EC and FEC and VC; EC and VC and VEC; FEC and PC and VC; FEC and EC and PC and VC.

Not specifically defined, the content of the cyclic carbonate is preferably within a range of from 10 to 40% by volume relative to the total volume of the nonaqueous solvent. When the content is less than 10% by volume, then the electric conductivity of the nonaqueous electrolytic solution may lower, and the low-temperature and high-temperature cycle properties may worsen; but when more than 40% by volume, then the low-temperature and high-temperature cycle properties and the load characteristics after high-temperature charging storage may worsen since the viscosity of the nonaqueous electrolytic solution may incerase. Consequently, the content preferably falls within the above-mentioned range.

The linear carbonates include asymmetric linear carbonates such as methyl ethyl carbonate (MEC), methyl propyl carbonate, methyl isopropyl carbonate, methyl butyl carbonate, ethyl propyl carbonate, etc.; symmetric linear carbonates such as dimethyl carbonate (DMC), diethyl carbonate (DEC), dipropyl carbonate, dibutyl carbonate, etc. From the viewpoint of improving the low-temperature cycle properties and improving the load characteristics after high-temperature charging storage, the solvent preferably contains a methyl group-having linear carbonate, more preferably DMC. From the viewpoint of improving the high-temperature cycle properties and improving the load characteristics after high-temperature charging storage, the solvent preferably contains an asymmetric carbonate, more preferably MEC.

Not specifically defined, the content of the linear carbonate is preferably within a range of from 60 to 90% by volume relative to the total volume of the nonaqueous solvent. When the content is less than 60% by volume, then the viscosity of the nonaqueous electrolytic solution may increase and the low-temperature cycle properties and the load characteristics after high-temperature charging storage may worsen. On the other hand, when the content is more than 90% by volume, then the electric conductivity of the nonaqueous electrolytic solution may lower, and the above-mentioned battery performance may thereby worsen. Consequently, the content preferably falls within the above-mentioned range.

The linear esters include methyl propionate, ethyl propionate, methyl acetate, ethyl acetate, methyl pivalate, butyl pivalate, hexyl pivalate, octyl pivalate, dimethyl oxalate, ethyl methyl oxalate, diethyl oxalate, etc. The lactones include γ-butyrolactone, γ-valerolactone, α-angelicalactone, etc.; the ethers include cyclic ethers such as tetrahydrofuran, 2-methyltetrahydrofuran, 1,3-dioxolane, 1,3-dioxane, 1,4-dioxane, etc.; and linear ethers such as 1,2-dimethoxyethane, 1,2-diethoxyethane, 1,2-dibutoxyethane, etc.

The amides include dimethylformamide, etc.; the phosphates include trimethyl phosphate, tributyl phosphate, trioctyl phosphate, etc.; the sulfones include sulfolane, etc.; the nitriles include acetonitrile, propionitrile, succinonitrile, glutaronitrile, adiponitrile, pimelonitrile, etc.

The S=O bond-containing compounds include sultone compounds such as 1,3-propanesultone, 1,3-butanesultone, 1,4-butanesultone, etc.; cyclic sulfite compounds such as ethylene sulfite, hexahydrobenzo[1,3,2]dioxathiol-2-oxide (also referred to as 1,2-cyclohexanediol cyclic sulfite), 5-vinyl-hexahydro-1,3,2-benzodioxathiol-2-oxide, etc.; sulfonic acid ester compounds such as 1,2-ethanediol dimethanesulfonate, 1,2-propanediol dimethanesulfonate, 1,3-propanediol dimethanesulfonate, 1,4-butanediol dimethanesulfonate, 1,5-pentanediol dimethanesulfonate, 2-propynyl methanesulfonate, methylenemethane disulfonate, etc.; and vinyl sulfone compounds such as divinyl sulfone, 1,2-bis(vinylsulfonyl)ethane, bis(2-vinylsulfonylethyl)ether, etc.

As other nonaqueous solvents, preferably used here are linear carboxylic acid anhydrides such as acetic anhydride, propionic anhydride, etc.; cyclic acid anhydrides such as succinic anhydride, maleic anhydride, glutaric anhydride, itaconic anhydride, 3-sulfo-propionic anhydride, etc.; cyclic phosphazene compounds such as methoxypentafluorocyclotriphosphazene, ethoxypentafluorocyclotriphosphazene, phenoxypentafluorocyclotriphosphazene, ethoxyheptafluorocyclotetraphosphazene, etc.; branched alkyl group-having aromatic compounds such as cyclohexylbenzene, fluorocyclohexylbenzene compounds (including 1-fluoro-2-cyclohexylbenzene, 1-fluoro-3-cyclohexylbenzene, and 1-fluoro-4-cyclohexylbenzene), tert-butylbenzene, tert-amylbenzene, 1-fluoro-4-tert-butylbenzene, etc.; and other aromatic compounds such as biphenyl, terphenyls (o-, m-, and p-form), diphenyl ether, fluorobenzene, difluorobenzenes (o-, m-, and p-form), anisole, 2,4-difluoroanisole, partially hydrogenated terphenyls (including 1,2-dicyclohexylbenzene, 2-phenylbicyclohexyl, 1,2-diphenylcyclohexane, and o-cyclohexylbiphenyl), etc.

In general, the above-mentioned nonaqueous solvents are combined and used as a mixture thereof for attaining suitable physical properties. The combination includes, for example, a combination of a cyclic carbonate and a linear carbonate, a combination of a cyclic carbonate, a linear carbonate and a lactone, a combination of a cyclic carbonate, a linear carbonate and an ether, a combination of a cyclic carbonate, a linear carbonate and a linear ester, a combination of a cyclic carbonate, a linear carbonate and a nitrile, a combination of a cyclic carbonate, a linear carbonate and an S=O bond-containing compound, etc.

Of those, preferred is use of a nonaqueous solvent of a combination of at least a cyclic carbonate and a linear carbonate, as improving the low-temperature and high-temperature cycle properties and the load characteristics after high-temperature charging storage. In this, the proportion of the cyclic carbonate and the linear carbonate is not specifically defined, but preferably, the ratio (by volume) of cyclic carbonate/linear carbonate is from 10/90 to 40/60, more preferably from 15/85 to 35/65, even more preferably from 20/80 to 30/70.

[Electrolyte Salt]

The electrolyte salt for use in the present invention includes lithium salts such as $LiPF_6$, $LiPO_2F_2$, $LiBF_4$, $LiClO_4$, etc.; linear fluoroalkyl group-having lithium salts such as $LiN(SO_2CF_3)_2$, $LiN(SO_2C_2F_5)_2$, $LiCF_3SO_3$, $LiC(SO_2CF_3)_3$, $LiPF_4(CF_3)_2$, $LiPF_3(C_2F_5)_3$, $LiPF_3(CF_3)_3$, $LiPF_3(iso-C_3F_7)_3$, $LiPF_5(iso-C_3F_7)$, etc.; cyclic fluoroalkylene chain-having lithium salts such as $(CF_2)_2(SO_2)_2NLi$, $(CF_2)_3(SO_2)_2NLi$, etc.; and lithium salts with an oxalate complex as the anion therein, such as lithium bis[oxalate-O,O']borate, lithium difluoro[oxalate-O,O']borate, etc. Of those, especially preferred electrolyte salts are $LiPF_6$, $LiBF_4$, $LiN(SO_2CF_3)_2$ and $LiN(SO_2C_2F_5)_2$. One alone or two or more of those electrolyte salts may be used here either singly or as combined.

A preferred combination of these electrolyte salts comprises $LiPF_6$ and contains at least one selected from $LiBF_4$, $LiN(SO_2CF_3)_2$ and $LiN(SO_2C_2F_6)_2$. Preferred are a combination of $LiPF_6$ and $LiBF_4$, a combination of $LiPF_6$ and $LiN(SO_2CF_3)_2$, a combination of $LiPF_6$ and $LiN(SO_2C_2F_6)_2$, etc.

Regarding the ratio (by mol) of $LiPF_6/[LiBF_4$ or $LiN(SO_2CF_3)_2$ or $LiN(SO_2C_2F_6)_2]$, when the ratio of $LiPF_6$ is lower than 70/30 and when the ratio of $LiPF_6$ is higher than 99/1, then the low-temperature and high-temperature cycle properties and the load characteristics after high-temperature charging storage may worsen. Accordingly, the ratio (by mol) of $LiPF_6/[LiBF_4$ or $LiN(SO_2CF_3)_2$ or $LiN(SO_2C_2F_6)_2]$ is preferably within a range of from 70/30 to 99/1, more preferably within a range of from 80/20 to 98/2. When the electrolyte salts are used as the combination thereof falling within the above-mentioned range, then the battery characteristics of the low-temperature and high-temperature cycle properties and the load characteristics after high-temperature charging storage and others can be further improved.

The concentration of all these electrolyte salts as dissolved in the solution is generally preferably at least 0.3 M relative to the above-mentioned nonaqueous solvent, more preferably at least 0.5 M, even more preferably at least 0.7 M, and further preferably at least 1.0 M. The upper limit of the concentration is preferably at most 2.5 M, more preferably at most 2.0 M, even more preferably at most 1.5 M.

As the electrolyte for electric double layer capacitors (condensers), usable are known quaternary ammonium salts such as tetraethylammonium tetrafluoroborate, triethylmethylammonium tetrafluoroborate, tetraethylammonium hexafluorophosphate, etc.

[Production of Nonaqueous Electrolytic Solution]

The nonaqueous electrolytic solution of the present invention can be prepared, for example, by: mixing the nonaqueous solvents; adding the electrolyte salt to the mixture; and adding thereto at least one alkynyl compound represented by the general formula (I) in an amount of from 0.01 to 10% by mass relative to the mass of the nonaqueous electrolytic solution.

In this case, the nonaqueous solvent to be used, and the compound to be added to the electrolytic solution are preferably previously purified within a range not significantly detracting from the producibility, in which, therefore, the impurity content is preferably as low as possible.

[Electrochemical Element]

The electrochemical element of the present invention comprises a positive electrode, a negative electrode, and a nonaqueous electrolytic solution of an electrolyte salt dissolved in a nonaqueous solvent, and is characterized in that the nonaqueous electrolytic solution is the above-mentioned nonaqueous electrolytic solution of the present invention. The electrochemical element includes the following first to fourth electrochemical elements.

As the nonaqueous electrolyte, not only a liquid one but also a gelled one can be used. Further, the nonaqueous electrolytic solution of the present invention can also be used for solid polymer electrolytes. Above all, the solution is preferably used for the first electrochemical element using a lithium salt as the electrolyte salt (that is, for lithium batteries) or for the fourth electrochemical element (that is, for lithium ion capacitors), more preferably for lithium batteries, and most preferably for lithium secondary batteries.

[The First Electrochemical Element (Lithium Battery)]

The lithium battery of the present invention collectively means a lithium primary battery and a lithium secondary battery. The lithium battery of the present invention comprises a positive electrode, a negative electrode and the nonaqueous electrolytic solution of an electrolyte salt dissolved in a nonaqueous solvent. In this, the other constitutive components such as the positive electrode and the negative electrode than the nonaqueous electrolytic solution can be used with no particular limitation thereon.

(Lithium Secondary Battery)

As the positive electrode active material for the lithium secondary battery, usable is a complex metal oxide with lithium that contains at least one selected from cobalt, manganese and nickel. One kind of these positive electrode active materials can be used alone, or two or more kinds of them can be used in combination.

The lithium complex metal oxide includes, for example, $LiCoO_2$, $LiMn_2O_4$, $LiNiO_2$, $LiCo_{1-x}Ni_xO_2$ ($0.01<x<1$), $LiCO_{1/3}Ni_{1/3}Mn_{1/3}O_2$, $LiNi_{1/2}Mn_{3/2}O_4$; $LiCo_{0.98}Mg_{0.02}O_2$ etc. Combinations of $LiCoO_2$ and $LiMn_2O_4$; $LiCoO_2$ and $LiNiO_2$; $LiMn_2O_4$ and $LiNiO_2$ are acceptable herein.

For improving the safety of the battery in overcharging or improving the cycle properties thereof, or for enabling the use thereof at a charging potential of 4.3 V or more, a part of the lithium complex metal oxide may be substituted with any other element. For example, a part of cobalt, manganese and nickel may be substituted with at least one element of Sn, Mg, Fe, Ti, Al, Zr, Cr, V, Ga, Zn, Cu, Bi, Mo, La, etc.; or O may be partly substituted with S or F; or the oxide may be coated with a compound containing such other element.

Of those, preferred are lithium complex metal oxides such as $LiCoO_2$, $LiMn_2O_4$ and $LiNiO_2$, with which the positive electrode charging potential in a fully-charged state may be used at 4.3 V or more based on Li. More preferred are lithium complex metal oxides usable at 4.4 V or more, such as $LiCo_{1-x}M_xO_2$ (where M represents at least one element of Sn, Mg, Fe, Ti, Al, Zr, Cr, V, Ga, Zn, and Cu; $0.001 \leq x \leq 0.05$), $LiCo_{1/3}Ni_{1/3}Mn_{1/3}O_2$, $LiNi_{1/2}Mn_{3/2}O_4$, and a solid solution of $Li_2MnO_3$ and $LiMO_2$ (where M represents a transition metal such as Co, Ni, Mn, Fe, etc.). When a lithium complex metal oxide capable of being used at a higher charged voltage is used, the effect of improving the low-temperature and high-temperature cycle properties and/or the load characteristics after high-temperature charging storage may often worsen owing to the reaction with the electrolytic solution during charging. Of the lithium secondary battery according to the present invention, however, the battery characteristics can be prevented from worsening.

Further, as the positive electrode active material, also usable are lithium-containing olivine-type phosphates. Especially preferred are lithium-containing olivine-type phosphates containing at least one selected from iron, cobalt, nickel and manganese. Specific examples thereof include $LiFePO_4$, $LiCoPO_4$, $LiNiPO_4$, $LiMnPO_4$, etc.

The lithium-containing olivine-type phosphates may be partly substituted with any other element. For example, a part of iron, cobalt, nickel, and manganese therein may be substituted with at least one element selected from Co, Mn, Ni, Mg, Al, B, Ti, V, Nb, Cu, Zn, Mo, Ca, Sr, W, Zr and the like; or the phosphates may be coated with a compound containing any of these other elements or with a carbon material. Among these, preferred are $LiFePO_4$ and $LiMnPO_4$.

Further, the lithium-containing olivine-type phosphate may be combined with, for example, the above-mentioned positive electrode active materials.

For the positive electrode for lithium primary batteries, there are mentioned oxides or chalcogen compounds of one or more metal elements such as CuO, $Cu_2O$, $Ag_2O$, $Ag_2CrO_4$, CuS, $CuSO_4$, $TiO_2$, $TiS_2$, $SiO_2$, SnO, $V_2O_5$, $V_6O_{12}$, $VO_x$, $Nb_2O_5$, $Bi_2O_3$, $Bi_2Pb_2O_5$, $Sb_2O_3$, $CrO_3$, $Cr_2O_3$, $MoO_3$, $WO_3$, $SeO_2$, $MnO_2$, $Mn_2O_3$, $Fe_2O_3$, FeO, $Fe_3O_4$, Ni$_2$O$_3$, NiO, CoO$_3$, CoO, etc.; sulfur compounds such as SO$_2$, SOCl$_2$, etc.; carbon fluorides (fluorographite) represented by a general formula (CF$_x$)$_n$, etc. Of those, preferred are MnO$_2$, V$_2$O$_5$, fluorographite, etc.

Not specifically defined, the electroconductive agent of the positive electrode may be any electron-conductive material not undergoing chemical change. For example, it includes graphites such as natural graphite (flaky graphite, etc.), artificial graphite, etc.; carbon blacks such as acetylene black, Ketjen black, channel black, furnace black, lamp black, thermal black, etc. Graphites and carbon blacks may be combined suitably for use herein. The amount of the electroconductive agent to be added to the positive electrode mixture is preferably from 1 to 10% by mass, more preferably from 2 to 5% by mass.

The positive electrode may be formed by mixing the above-mentioned positive electrode active material with an electroconductive agent such as acetylene black, carbon black or the like, and with a binder such as polytetrafluoroethylene (PTFE), polyvinylidene fluoride (PVDF), styrene/butadiene copolymer (SBR), acrylonitrile/butadiene copolymer (NBR), carboxymethyl cellulose (CMC), ethylene/propylene/diene terpolymer or the like, then adding thereto a high-boiling point solvent such as 1-methyl-2-pyrrolidone or the like, and kneading them to give a positive electrode mixture, thereafter applying the positive electrode mixture onto an aluminium foil or a stainless lath plate or the like serving as a collector, and drying and shaping it under pressure, and then heat-treating it in vacuum at a temperature of from 50° C. to 250° C. or so for about 2 hours.

The density of the part except the collector of the positive electrode may be generally at least 1.5 g/cm$^3$, and for further increasing the capacity of the battery, the density is preferably at least 2 g/cm$^3$, more preferably at least 3 g/cm$^3$, even more preferably at least 3.6 g/cm$^3$. The upper limit is preferably at most 4 g/cm$^3$.

As the negative electrode active material for the lithium secondary battery, usable are one or more of lithium metal, lithium alloys, carbon materials capable of absorbing and releasing lithium [graphatizable carbon, non-graphatizable carbon where the lattice (002) spacing is at least 0.37 nm, graphite where the lattice (002) spacing is at most 0.34 nm, etc.], tin, tin compounds, silicon, silicon compounds and the like, either singly or as combined.

Of those, more preferred is use of high-crystalline carbon materials such as artificial graphite, natural graphite and the like, in view of the ability thereof to absorb and release lithium ions, and even more preferred is use of a carbon material having a graphite-type crystal structure where the lattice (002) spacing (d$_{002}$) is at most 0.340 nm, especially from 0.335 to 0.337 nm.

When artificial graphite particles having a bulky structure where plural flattened graphite fine particles aggregate or bond together non-parallel to each other, or graphite particles produced through spheroidizing treatment comprising repeatedly imparting mechanical action such as compression force, friction force, shear force or the like to, for example, flaky natural graphite particles are used, and when the ratio of the peak intensity I (110) of the (110) plane of the graphite crystal obtained in X-ray diffractiometry of a negative electrode sheet as formed by pressing so that the density of the part except the collector of the negative electrode could be 1.5 g/cm$^3$ or more, to the peak intensity I (004) of the (004) plane thereof, I(110)/I(004) is at least 0.01, then the low-temperature and high-temperature cycle properties could be favorably bettered, and more preferably, the ratio is at least 0.05, even more preferably at least 0.1. On the other hand, when too much processed, then the crystallinity may worsen and the discharge capacity of the battery may lower; and therefore, the upper limit is at most 0.5, more preferably at most 0.3.

Preferably, the high-crystalline carbon material is coated with a low-crystalline carbon material, as bettering the low-temperature and high-temperature cycle properties. When the high-crystalline carbon material is used, it may readily react with the nonaqueous electrolytic solution in charging to thereby worsen the low-temperature and high-temperature cycle properties owing to the increase in the interfacial resistance; however, in the lithium secondary battery of the present invention, the low-temperature and high-temperature cycle properties can be bettered.

The metal compound capable of absorbing and releasing lithium, serving as a negative electrode active material, includes compounds containing at least one metal element of Si, Ge, Sn, Pb, P, Sb, Bi, Al, Ga, In, Ti, Mn, Fe, Co, Ni, Cu, Zn, Ag, Mg, Sr, Ba, etc. These metal compounds may have any morphology of simple substances, alloys, oxides, nitrides, sulfides, borides, alloys with lithium or the like; but preferred are any of simple substances, alloys, oxides and alloys with lithium, as capable of increasing the battery capacity. Above all, more preferred are those containing at least one element selected from Si, Ge and Sn, and even more preferred are those containing at least one element selected from Si and Sn, as capable of increasing the battery capacity.

The negative electrode may be formed, using the same electroconductive agent, binder and high-boiling point solvent as in the formation of the above-mentioned positive electrode. These are mixed and kneaded to give a negative electrode mixture, then the negative electrode mixture is applied onto a copper foil or the like serving as a collector, then dried and shaped under pressure, and thereafter heat-treated in vacuum at a temperature of from 50° C. to 250° C. or so for about 2 hours.

The density of the part except the collector of the negative electrode may be generally at least 1.1 g/cm$^3$, and for further increasing the battery capacity, the density is preferably at least 1.5 g/cm$^3$, more preferably at least 1.7 g/cm$^3$. The upper limit is preferably at most 2 g/cm$^3$.

As the negative electrode active material for lithium primary batteries, usable are lithium metal or lithium alloys.

The structure of the lithium battery is not specifically defined. The battery may be a coin-shaped battery, a cylindrical battery, a square-shaped battery, a laminate-type battery or the like, each having a single-layered or multi-layered separator.

For the separator for the battery, usable is a single-layer or laminate porous film of polyolefin such as polypropylene, polyethylene or the like, as well as a woven fabric, a nonwoven fabric, etc.

The lithium secondary battery of the present invention has excellent low-temperature and high-temperature cycle properties even when the final charging voltage is 4.2 V or more, especially 4.3 v or more, and further, the properties of the battery are still good even at 4.4 V or more. The discharging final voltage could be generally 2.8 V or more, further 2.5 V or more; however, the discharging final voltage of the lithium secondary battery of the present invention could can be 2.0 V or more. The current value is not specifically defined, but in general, the battery is used within a range of from 0.1 to 3 C. The lithium battery of the present invention can be charged/discharged at −40 to 100° C., preferably at −10 to 80° C.

In the present invention, as a countermeasure against the increase in the internal pressure of the lithium battery, there may be employed a method of providing a safety valve in the battery cap or a method of forming a cutout in the battery component such as the battery can, the gasket or the like. In addition, as a safety countermeasure against overcharging, a current breaker capable of detecting the internal pressure of the battery to cut off the current may be provided in the battery cap.

(Lithium Primary Battery)

The constitution of the lithium primary battery is not specifically defined. Except for the constitution peculiar to lithium primary batteries, the constitution of the lithium primary battery of the present invention can be the same as that of the above-mentioned lithium secondary battery.

For the positive electrode for the lithium primary battery, there are mentioned oxides or chalcogen compounds of one or more metal elements such as CuO, $Cu_2O$, $Ag_2O$, $Ag_2CrO_4$, CuS, $CuSO_4$, $TiO_2$, $TiS_2$, $SiO_2$, SnO, $V_2O_5$, $V_6O_{12}$, $VO_x$, $Nb_2O_5$, $Bi_2O_3$, $Bi_2Pb_2O_5Sb_2O_3$, $CrO_3$, $Cr_2O_3$, $MoO_3$, $WO_3$, $SeO_2$, $MnO_2$, $Mn_2O_3$, $Fe_2O_3$, FeO, $Fe_3O_4$, $Ni_2O_3$, NiO, $CoO_3$, CoO, etc.; sulfur compounds such as $SO_2$, $SOCl_2$, etc.; carbon fluorides (fluorographite) represented by a general formula $(CF_x)_n$, etc. Of those, preferred are $MnO_2$, $V_2O_5$, fluorographite, etc.

As the negative electrode active material for the lithium primary battery, usable are lithium metal, lithium alloys, etc.

[The Second Electrochemical Element (Electric Double-Layer Capacitor)]

This is an electrochemical element that stores energy by utilizing the electric double layer capacitance in the interface between the electrolytic solution and the electrode therein. One example of the present invention is an electric double layer capacitor. The most typical electrode active material to be used in the electrochemical element is active carbon.

[The Third Electrochemical Element]

This is an electrochemical element that stores energy by utilizing the doping/dedoping reaction of the electrode therein. As the electrode active material for use in the electrochemical element, there may be mentioned metal oxides such as ruthenium oxide, iridium oxide, tungsten oxide, molybdenum oxide, copper oxide, etc.; n-conjugated polymers such as polyacene, polythiophene derivatives, etc.

[The Fourth Electrochemical Element (Lithium Ion Capacitor)]

This is an electrochemical element that stores energy by utilizing the lithium ion intercalation into the carbon material such as graphite or the like of the negative electrode therein. This may be referred to as a lithium ion capacitor (LIC). As the positive electrode, for example, there may be mentioned one that utilizes the electric double layer between the active carbon electrode and the electrolytic solution therein, or one that utilizes the doping/dedoping reaction of the n-conjugated polymer electrode therein. The electrolytic solution contains at least a lithium salt such as $LiPF_6$ or the like.

[Alkynyl Compound]

The alkynyl compound of the present invention is represented by the following general formula (II):

[Chemical Formula 9]

(II)

(In the formula, $X^2$ represents a group $—S(=O)_2—$, or a group $—X^3—S(=O)_2O—$
(where $X^3$ represents an alkylene group having from 1 to 8 carbon atoms, or a divalent linking group having from 2 to 8 carbon atoms and containing at least one ether bond). $R^4$ represents an alkenyl group having from 2 to 8 carbon atoms or an alkenyloxy group having from 2 to 8 carbon atoms; and $R^5$ represents an alkynyl group having from 3 to 8 carbon atoms, or an alkynyloxy group having from 3 to 8 carbon atoms.)

In the general formula (II), specific examples and preferred examples of $X^2$, $R^4$ and $R^5$ are the same as those mentioned hereinabove for the general formula (I).

The alkynyl compound represented by the general formula (II) can be produced according to the following method, to which, however, the present invention is not limited. The starting material, 1,2-ethanedisulfonic acid dichloride can be produced according to already-existing general methods, to which, for example, applicable is the method described in Journal of Fluorine Chemistry, 1995, Vol. 75 (1), pp. 61-66.

As the production method for the alkynyl compound, there may be mentioned a method of reacting 1,2-diethanedisulfonic acid dichloride with an alcohol in a solvent or in the absence of a solvent and in the presence of a base.

In producing the alkynyl compound, the amount of the alcohol to be reacted with 1,2-diethanedisulfonic acid dichloride is preferably from 1.8 to 20 mol relative to 1 mol of 1,2-diethanedisulfonic acid dichloride, more preferably from 2 to 6 mol, most preferably from 2 to 3 mol.

The alcohol to be used includes 2-propyn-1-ol, 1-methyl-2-propyn-1-ol, 1,1-dimethyl-2-propyn-1-ol, 2-butyn-1-ol, 3-butyn-1-ol, etc. Above all, preferred are 2-propyn-1-ol, 1-methyl-2-propyn-1-ol and 1,1-dimethyl-2-propyn-1-ol that are industrially inexpensive.

Not specifically defined, the solvent to be used for the production is any one inert to the reaction. Preferred are aliphatic hydrocarbons such as hexane, heptane, etc.; halogenohydrocarbons such as dichloroethane, dichloropropane, etc.; aromatic hydrocarbons such as toluene, xylene, etc.; halogenoaromatic hydrocarbons such as chlorobenzene, fluorobenzene, etc.; ethers such as diethyl ether, etc.; nitriles such as acetonitrile, propionitrile, etc.; amides such as N,N-dimethylformamide, etc.; sulfoxides such as dimethyl sulfoxide, etc.; nitroalkanes such as nitromethane, nitroethane, etc.; esters such as ethyl acetate, dimethyl carbonate, etc.; and their mixtures. Especially preferred for use herein are toluene, xylene and ethyl acetate. The amount of the solvent to be used is preferably from 0 to 30 parts by mass relative to 1 part by mass of 1,2-ethanedisulfonic acid dichloride, more preferably from 1 to 15 parts by mass.

As the base for use for the production, any of an inorganic base or an organic base is usable. These may be used either singly or as combined. The usable inorganic base includes potassium carbonate, sodium carbonate, calcium hydroxide, and calcium oxide. The usable organic base includes linear or branched aliphatic tertiary amines, and unsubstituted or substituted imidazole, pyridine and pyrimidine. More preferred are trialkylamines such as trimethylamine, triethylamine, tripropylamine, tributylamine, ethyldiisopropylamine, etc.; and pyridines such as pyridine, N,N-dimethylaminopyridine, etc. The amount of the base to be used may be from 1.6 to 20 mol relative to 1 mol of 1,2-ethanedisulfonic acid dichloride, more preferably from 2 to 10 mol, and when the amount is from 2 to 6 mol, the production of side products can be prevented.

In the reaction of alcohol and 1,2-ethanedisulfonic acid dichloride, the lower limit of the reaction temperature is preferably −20° C. or higher, and is more preferably −10° C. or higher so as not to lower the reactivity. The upper limit of the reaction temperature is preferably 80° C. or lower, and when higher than this, side reaction may occur and the product may be decomposed more, and therefore the reaction temperature is more preferably not higher than 60° C. The reaction time may vary depending on the reaction temperature and the scale, however, when the reaction time is too short, then unreacted matters may remain, but on the contrary, when the reaction time is too long, the product may be decomposed and side reaction may occur. Preferably, therefore, the reaction time is from 0.1 to 12 hours, more preferably from 0.2 to 6 hours.

[Alkynyl Sulfonate Compound]

The alkynyl sulfonate compound of the present invention is represented by the following general formula (III):

[Chemical Formula 10]

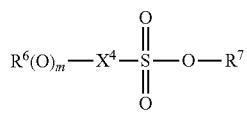

(III)

(In the formula, $X^4$, $R^6$ and $R^7$ have the same meanings as mentioned above.)

In the general formula (III), specific examples and preferred examples of $X^4$, $R^6$ and $R^7$ are the same as those mentioned hereinabove for the general formula (III).

The alkynyl sulfonate compound represented by the general formula (III) can be produced according to the following methods (i) to (vi) or the like, to which, however, the present invention is not limited.

(i) A method where a hydroxysulfonate is condensed with formic acid in the presence or absence of a solvent and in the presence or absence of an acid catalyst and optionally in the presence of a dehydrating agent.

(ii) A method where a hydroxysulfonate is interesterified with a formate in the presence or absence of a solvent and in the presence of an acid catalyst.

(iii) A method where a hydroxysulfonate is esterified with an acid anhydride or a mixed acid anhydride in the presence or absence of a solvent.

(iv) A method where an acyloxysulfonic acid halide is esterified with propargyl alcohol in the presence or absence of a solvent and in the presence of a base.

(v) A method where a sulfonic acid salt is esterified with a propargyl halide in the presence or absence of a solvent.

(vi) A method where an acyloxysulfonate is reacted with an alcohol in the presence or absence of a solvent and in the presence of a base.

EXAMPLES

Synthesis Examples of the compounds of the present invention, and Examples of the lithium ion secondary batteries using the nonaqueous electrolytic solution of the present invention are shown below. However, the present invention is not limited to these Synthesis Examples and Examples.

Synthesis Example I-1

Synthesis of 2-propynyl vinyl sulfonate 8.14 g (34.8 mmol) of disodium 1,2-ethanedisulfonate and 17.38 g (83.5 mmol) of phosphorus pentachloride were stirred at 90° C. for 3 hours. After the reaction, this was cooled to 5° C., 30 ml of water was carefully added to the reaction product and filtered, and the filtrate was concentrated under reduced pressure to give 8.31 g of 1,2-ethanedisulfonic acid dichloride.

3.08 g (54.9 mmol) of propargyl alcohol and 4.95 g (48.9 mmol) of triethylamine were dissolved in 30 ml of ethyl acetate, and cooled to 6° C. 5.00 g (22.0 mmol) of 1,2-ethanedisulfonic acid dichloride was dropwise added to the solution at 0 to 6° C., taking 30 minutes, and stirred at room temperature for 1 hour and 30 minutes. After the reaction, 30 ml of water was added thereto for liquid-liquid separation, the organic layer was washed with 60 ml of a saturated saline solution, and the solvent was distilled away under reduced pressure. The residue was purified through silica gel column chromatography (elution with ethyl acetate/hexane=1/1) to give 1.47 g of 2-propynyl vinylsulfonate (yield: 29%).

The obtained 2-propynyl vinylsulfonate was analyzed for $^1$H-NMR and mass spectrometry, and the results are shown below.

(1) $^1$H-NMR (300 MHz, CDCl$_3$): δ=6.67-6.59 (m, 1H), 6.48-6.43 (m, 1H), 6.21-6.17 (m, 1H), 4.78 (s, 2H), 2.68 (s, 1H).

(2) Mass spectrometry: MS (CI) m/z [M+1]=147.

Examples I-1 to I-10, and Comparative Examples I-1 to I-2

(1) Production of Lithium Ion Secondary Battery

93% by mass of LiCoO$_2$ (positive electrode active material) and 3% by mass of acetylene black (electroconductive agent) were mixed, and added to and mixed in a solution previously prepared by dissolving 4% by mass of polyvinylidene fluoride (binder) in 1-methyl-2-pyrrolidone, thereby preparing a positive electrode mixture paste. The positive electrode mixture paste was applied on both surfaces of an aluminium foil (collector), then dried, processed under pressure and cutted into a predetermined size, thereby producing a positive electrode sheet. The density of the part of the positive electrode except the collector was 3.6 g/cm$^3$.

On the other hand, 95% by mass of artificial graphite coated with low-crystalline carbon (d$_{002}$=0.335 nm, negative electrode active material) was added to and mixed in a solution previously prepared by dissolving 5% by mass of polyvinylidene fluoride (binder) in 1-methyl-2-pyrrolidone, thereby preparing a negative electrode mixture paste. The negative electrode mixture paste was applied onto both surfaces of a copper foil (collector), dried, processed under pressure and cutted into a predetermined size, thereby producing a negative electrode sheet. The density of the part of the negative electrode except the collector was 1.7 g/cm$^3$.

The positive electrode sheet, a porous polyethylene film separator, the negative electrode sheet and the separator were laminated in that order, and the resulting laminate was coiled up. The coil was housed in a nickel-plated, iron-made cylindrical battery can serving also as a negative electrode terminal.

Next, a nonaqueous electrolytic solution prepared by adding thereto a predetermined amount of the compound shown in Table 1 was injected into the battery can, then a battery cap having a positive electrode terminal was caulked with a gasket, thereby constructing a 18650-type cylindrical battery. In this, the positive electrode terminal was previously interconnected inside the battery, using the positive electrode sheet and an aluminium lead tab, and the negative electrode can was also inside the battery, using the negative electrode sheet and a nickel lead tab.

The structure of the compound given in Table 1 is as shown below.

[Chemical Formula 11]

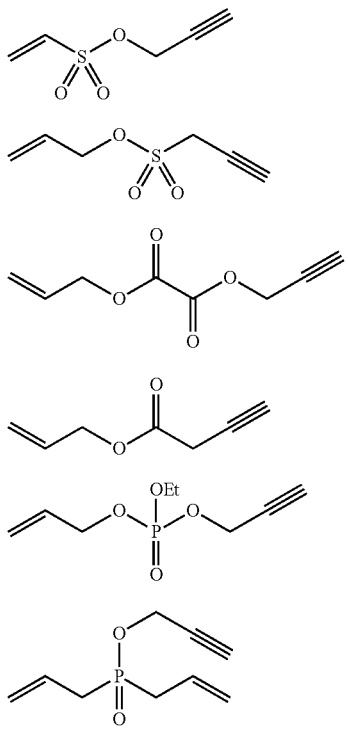

(2) Evaluation of Low-Temperature Cycle Properties

In a thermostatic chamber kept at 25° C., the battery fabricated according to the above-mentioned method was charged up to 4.2 V (charging final voltage) with a constant current of 1 C, then charged for 2.5 hours under a constant voltage of 4.2 V, and thereafter discharged under a constant current of 1 C to a discharging voltage of 3.0 V (discharging final voltage). Next, in a thermostatic chamber at 0° C., this was charged up to 4.2 V with a constant current of 1 C, then charged for 2.5 hours under a constant voltage of 4.2 V, and thereafter discharged under a constant current of 1 C to a discharging voltage of 3.0 V. The cycle was repeated up to 50 cycles. According to the formula mentioned below, the discharge capacity retention rate (%) after 50 cycles at 0° C. was calculated. The results are shown in Table 1.

0° C. Discharge Capacity Retention Rate after 50 cycles (%)=[(discharge capacity at 0° C. at 50th cycle/discharge capacity at 0° C. at 1st cycle)×100.

(3) Evaluation of High-Temperature Cycle Properties

In a thermostatic chamber kept at 60° C., the battery fabricated according to the above-mentioned method was charged up to 4.2 V (charging final voltage) with a constant current of 1 C, then charged for 2.5 hours under a constant voltage of 4.2 V, and thereafter discharged under a constant current of 1 C to a discharging voltage of 3.0 V (discharging final voltage). The cycle was repeated up to 100 cycles. According to the formula mentioned below, the discharge capacity retention rate (%) after 100 cycles at 60° C. was calculated. The results are shown in Table 1.

60° C. Discharge Capacity Retention Rate after 100 cycles (%)=[(discharge capacity at 60° C. at 100th cycle/discharge capacity at 60° C. at 1st cycle)×100.

(4) Evaluation of Storage Properties

In a thermostatic chamber kept at 25° C., the cylindrical battery fabricated according to the above-mentioned method was charged up to a final voltage of 4.3 V for 3 hours with a constant current of 1 C and under a constant voltage, and then discharged to a final voltage of 3.0 V with a constant current of 1 C. The average discharging voltage during the discharging is the average discharging voltage before storage. Again this was charged up to a final voltage of 4.3 V for 3 hours with a constant current of 1 C and under a constant voltage, then put into a thermostatic chamber at 60° C., and while kept at 4.3 V, this was stored for 3 days. Subsequently, this was put into a thermostatic chamber at 25° C., then once discharged to a final voltage of 3.0 V under a constant current of 1 C, and again charged up to a final voltage of 4.3 V for 3 hours with a constant current of 1 C and under a constant voltage, and then discharged to a final voltage of 3.0 V under a constant current of 1 C. The average discharging voltage during the discharging is the average discharging voltage after storage. With that, a cylindrical battery was fabricated in the same manner as in Example I-1 except that the alkynyl compound represented by the general formula (I) was not added to the nonaqueous electrolytic solution therein, and evaluated for the battery characteristics as Comparative Example I-1. According to the formula mentioned below, as based on the value of the Comparative Example I-1, the average discharging voltage reduction rate after storage was calculated.

Average Discharging Voltage Reduction Rate (relative value) (%)=(average discharging voltage before storage−average discharging voltage after storage)/(average discharging voltage before storage in Comparative Example I-1−average discharging voltage after storage in Comparative Example I-1)×100.

The condition in producing the cylindrical batteries and the battery characteristics are shown in Table 1.

TABLE 1

| | Composition of Electrolyte Salt Composition of Nonaqueous Electrolytic Solution (ratio by volume of solvents) | Compound [Compound Number] | Added Amount *1 (% by mass) | 0° C. Discharge Capacity Retention Rate after 50 cycles (%) | 60° C. Discharge Capacity Retention Rate after 100 cycles (%) | Average Discharging Voltage Reduction Rate after high-temperature storage *2 (%) |
|---|---|---|---|---|---|---|
| Example I-1 | 1.1M LiPF$_6$ EC/FEC/MEC/DMC (15/15/30/40) | 2-propynyl vinylsulfonate [1] | 0.1 | 75 | 78 | 79 |

TABLE 1-continued

| | Composition of Electrolyte Salt Composition of Nonaqueous Electrolytic Solution (ratio by volume of solvents) | Compound [Compound Number] | Added Amount *1 (% by mass) | 0° C. Discharge Capacity Retention Rate after 50 cycles (%) | 60° C. Discharge Capacity Retention Rate after 100 cycles (%) | Average Discharging Voltage Reduction Rate after high-temperature storage *2 (%) |
|---|---|---|---|---|---|---|
| Example I-2 | 1.1M LiPF$_6$ EC/FEC/MEC/DMC (15/15/30/40) | | 1 | 81 | 88 | 70 |
| Example I-3 | 1.1M LiPF$_6$ EC/FEC/MEC/DMC (15/15/30/40) | | 3 | 80 | 86 | 71 |
| Example I-4 | 1.1M LiPF$_6$ EC/FEC/MEC/DMC (15/15/30/40) | | 7 | 77 | 84 | 75 |
| Example I-5 | 1.1M LiPF$_6$ EC/FEC/MEC/DMC (15/15/30/40) | 2-propenyl 2-propyne-1-sulfonate [2] | 1 | 80 | 86 | 72 |
| Example I-6 | 1.1M LiPF$_6$ EC/FEC/MEC/DMC (15/15/30/40) | 2-propenyl 2-propynyl oxalate [3] | 1 | 80 | 85 | 73 |
| Example I-7 | 1.1M LiPF$_6$ EC/FEC/MEC/DMC (15/15/30/40) | 2-propenyl 3-butynoate [4] | 1 | 78 | 85 | 75 |
| Example I-8 | 1.1M LiPF$_6$ EC/FEC/MEC/DMC (15/15/30/40) | ethyl 2-propenyl 2-propynyl phosphate [5] | 1 | 76 | 86 | 77 |
| Example I-9 | 1.1M LiPF$_6$ EC/FEC/MEC/DMC (15/15/30/40) | 2-propynyl di(2-propenyl)phosphinate [6] | 1 | 75 | 85 | 78 |
| Example I-10 | 1.1M LiPF$_6$ FEC/PC/VC/DMC (20/8/2/70) | 2-propynyl vinylsulfonate [1] | 1 | 83 | 89 | 68 |
| Comparative Example I-1 | 1.1M LiPF$_6$ EC/FEC/MEC/DMC (15/15/30/40) | none | — | 65 | 68 | 100 |
| Comparative Example I-2 | 1.1M LiPF$_6$ EC/FEC/MEC/DMC (15/15/30/40) | 2-propenyl 2-propynyl carbonate | 1 | 68 | 70 | 101 |

*1: content in nonaqueous electrolytic solution
*2: relative value

Example I-11, Comparative Example I-3

A positive electrode sheet was produced by changing the positive electrode active material used in Example I-1 to LiFePO$_4$ coated with amorphous carbon (positive electrode active material). Concretely, 90% by mass of LiFePO$_4$ coated with amorphous carbon and 5% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a positive electrode mixture paste.

The positive electrode mixture paste was applied onto an aluminium foil (collector), dried, processed under pressure and cutted into a predetermined size, thereby producing a belt-like positive electrode sheet. Using the nonaqueous electrolytic solution having the composition shown in Table 2, cylindrical batteries were produced and evaluated in the same manner as in Example I-1, except that the positive electrode sheet thus produced herein was used, that the charging final voltage was changed to 3.6 V and that the discharging final voltage was changed to 2.0 V. The results are shown in Table 2.

TABLE 2

| | Composition of Electrolyte Salt Composition of Nonaqueous Electrolytic Solution (ratio by volume of solvents) | Compound [Compound Number] | Added Amount *1 (% by mass) | 0° C. Discharge Capacity Retention Rate after 50 cycles (%) | 60° C. Discharge Capacity Retention Rate after 100 cycles (%) | Average Discharging Voltage Reduction Rate after high-temperature storage *2 (%) |
|---|---|---|---|---|---|---|
| Example I-11 | 1.1M LiPF$_6$ EC/FEC/MEC/DMC (15/15/30/40) | 2-propynyl vinylsulfonate [1] | 1 | 85 | 87 | 70 |
| Comparative Example I-3 | 1.1M LiPF$_6$ EC/FEC/MEC/DMC (15/15/30/40) | none | — | 67 | 74 | 100 |

*1: content in nonaqueous electrolytic solution
*2: relative value

Example I-12, Comparative Example I-4

A negative electrode sheet was produced, using silicon (negative electrode active material) in place of the negative electrode active material used in Example I-1. Precisely, 80% by mass of silicon and 15% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a negative electrode mixture paste.

The negative electrode mixture paste was applied onto a copper foil (collector), dried, processed under pressure, and cutted into a predetermined size, thereby producing a belt-like negative electrode sheet. Using the nonaqueous electrolytic solution having the composition shown in Table 3, cylindrical batteries were produced and evaluated in the same manner as in Example I-1, except that the negative electrode sheet produced herein was used. The results are shown in Table 3.

TABLE 3

|  | Composition of Electrolyte Salt Composition of Nonaqueous Electrolytic Solution (ratio by volume of solvents) | Compound [Compound Number] | Added Amount *1 (% by mass) | 0° C. Discharge Capacity Retention Rate after 50 cycles (%) | 60° C. Discharge Capacity Retention Rate after 100 cycles (%) | Average Discharging Voltage Reduction Rate after high-temperature storage *2 (%) |
|---|---|---|---|---|---|---|
| Example I-12 | 1.1M LiPF6 EC/FEC/MEC/DMC (15/15/30/40) | 2-propynyl vinylsulfonate [1] | 1 | 78 | 65 | 72 |
| Comparative Example I-4 | 1.1M LiPF6 EC/FEC/MEC/DMC (15/15/30/40) | none | — | 65 | 43 | 100 |

*1: content in nonaqueous electrolytic solution
*2: relative value

The lithium secondary batteries of Examples I-1 to I-10 were all remarkably bettered in point of the low-temperature and high-temperature cycle properties thereof, as compared with the lithium secondary battery of Comparative Example I-1 (in which the compound of the present invention was not added), and the lithium secondary battery of Comparative Example I-2 (in which a carbonate compound was used). From the results, it is known that the structure in which the alkenyl group and the alkynyl group are bonded to each other via a specific group selected from a group —C(═O)—, a group —C(═O)—C(═O)—, a group —S(═O)$_2$— and a group —P(═O)(—R$^3$)— brings about the unexpected specific effect.

In addition, from comparison between Example I-11 and Comparative Example I-3, and from comparison between Example I-12 and Comparative Example I-4, the same effect is seen in the case where a lithium-containing olivine-type iron phosphate was used as the positive electrode, and in the case where Si was used as the negative electrode. Accordingly, it is known that the effect of the present invention does not depend on any specific positive electrode or negative electrode.

Synthesis Example II-1

2-propynyl 2-(acetyloxy)ethanesulfonate 45.65 g (299 mmol) of sodium 2-hydroxyethanesulfonate having a purity of 97% was suspended in 70 mL of acetic anhydride, and heated under reflux for 5 hours. After the reaction, this was cooled to room temperature and concentrated under reduced pressure, and the precipitated crystal was washed with 100 mL of diethyl ether to give 52.0 g of sodium 2-(acetyloxy)ethanesulfonate (yield 91%).

52.00 g (273 mmol) of the obtained sodium 2-(acetyloxy) ethanesulfonate was suspended in 51.23 g (409 mmol) of thionyl chloride, and heated with stirring at 60° C. to 64° C. for 5 hours. After the reaction, the precipitated sodium chloride was removed through filtration, and the filtrate was concentrated under reduced pressure to give 32.63 g of 2-(acetyloxy)ethanesulfonyl chloride (yield 64%).

24.89 g (133 mmol) of the obtained 2-(acetyloxy)ethanesulfonyl chloride and 7.45 g (133 mmol) of propargyl alcohol were dissolved in 100 mL of dimethyl carbonate and cooled to 0° C. 13.45 g (133 mmol) of triethylamine was dropwise added to the solution at 0 to 5° C., taking 30 minutes, and then stirred for 1 hour at room temperature. After the reaction, 50 mL of water was added thereto, and extracted with 100 mL of dimethyl carbonate. The organic layer was dried with magnesium sulfate, and the solvent was evaporated away under reduced pressure. The obtained residue was purified through column chromatography (Wakogel C-200, elution with ethyl acetate/hexane=1/2 (v/v)) to give 13.16 g (yield 48) of 2-propynyl 2-acetyloxyethanesulfonate.

The $^1$H-NMR data (with JEOL's "AL 300") of the obtained 2-propynyl 2-acetyloxyethanesulfonate are shown below.

$^1$H-NMR (300 MHz, CDCl$_3$): δ=4.88 (d, J=2.69 Hz, 2H), 4.52 (t, J=6.10 Hz, 2H), 3.57 (t, J=6.10 Hz, 2H), 2.75 (m, 1H), 2.11 (s, 3H).

Synthesis Example II-2

2-propynyl 2-methoxyethanesulfonate 3.30 g (16 mmol) of 2-propynyl 2-(acetyloxy)ethanesulfonate obtained according to the same production method as in Synthesis Example II-1 was dissolved in 10 mL of methanol, and 2.20 g (16 mmol) of potassium carbonate was added thereto and stirred at room temperature for 1 hour. After the reaction, methanol was evaporated away under reduced pressure, 10 mL of water was added to the residue, and extracted with 20 mL of ethyl acetate. The organic layer was dried with magnesium sulfate, and the solvent was evaporated away under reduced pressure. The obtained residue was purified through column chromatography (Wakogel C-200, elution with ethyl acetate/hexane=1/2 (v/v)) to give 2.59 g (yield 91%) of 2-propynyl 2-methoxyethaneslfonate.

The $^1$H-NMR data of the obtained 2-propynyl 2-methoxyethaneslfonate are shown below.

$^1$H-NMR (300 MHz, CDCl$_3$): δ=4.86 (d, J=2.68 Hz, 2H), 3.84 (t, J=6.22 Hz, 2H), 3.49 (t, J=6.22 Hz, 2H), 3.40 (s, 3H), 2.69 (t, J=2.40 Hz, 1H).

Synthesis Example II-3

Synthesis of 2-propynyl 3-(methanesulfonyloxy)propanesulfonate 5.61 g (28 mmol) of 3-(acetyloxy)propanesulfonyl chloride obtained according to the same production method as in Synthesis Example II-1 and 1.57 g (28 mmol) of propargyl alcohol were dissolved in 50 mL of dimethyl carbonate, and cooled to 0° C. 2.83 g (28 mmol) of triethylamine was dropwise added to the solution at 0 to 5° C., taking 30 minutes, and then stirred at room temperature for 1.5 hours. After the reaction, 20 mL of water was added thereto and extracted with ethyl acetate. The organic layer was dried with magnesium sulfate, and the solvent was evaporated away under reduced pressure to give 5.37 g of 2-propynyl 3-(acetyloxy)propanesulfonate (yield 87%).

8.59 g (39 mmol) of the obtained 2-propynyl 3-(acetyloxy) propanesulfonate was dissolved in methanol, 5.36 g (39 mmol) of potassium carbonate was added thereto, and stirred at room temperature for 1 hour. After the reaction, 20 mL of water was added thereto, and extracted with 40 mL of ethyl acetate. The organic layer was dried with magnesium sulfate, and the solvent was evaporated away under reduced pressure to give 2.43 g of 2-propynyl 3-hydroxypropanesulfonate (yield 35%).

1.80 g (110 mmol) of the obtained 2-propynyl 3-hydroxypropanesulfonate and 0.98 g (12 mmol) of pyridine were dissolved in 15 mL of ethyl acetate, and cooled to 0° C. 1.39 g (12 mmol) of methanesulfonyl chloride was dropwise added to the solution at 0 to 5° C., taking 10 minutes, and stirred at 0° C. for 15 minutes. After the reaction, 10 mL of water was added thereto and extracted with ethyl acetate. The organic layer was dried with magnesium sulfate, and the solvent was evaporated away under reduced pressure. The obtained residue was purified through column chromatography (Wakogel C-200, elution with ethyl acetate/hexane=3/4 (v/v)) to give 0.64 g of the intended 2-propynyl 3-(methanesulfonyloxy)propanesulfonate (yield: 25%).

The $^1$H-NMR data of the obtained 2-propynyl 3-(methanesulfonyloxy)propanesulfonate are shown below.

$^1$H-NMR (300 MHz, CDCl$_3$): δ=4.88 (d, J=2.44 Hz, 2H), 4.39 (t, J=6.10 Hz, 2H), 3.41 (t, J=7.07, 2H), 3.05 (s, 3H), 2.74 (t, J=2.44 Hz, 1H), 2.41-2.32 (m, 2H).

Synthesis Example II-4

Synthesis of di(2-propynyl)ethane-1,2-disulfonate 7.54 g (40 mmol) of ethane-1,2-disulfonic acid was dissolved in a mixed solvent of dioxane 90 ml and acetonitrile 60 ml, and 20.20 g (87 mmol) of silver(II) oxide was added to the solution and stirred at room temperature for 12 hours. The reaction liquid was filtered, the filtrated residue was washed with 50 mL of water, and the filtrate was concentrated under reduced pressure. The residue was dissolved in 60 mL of water, and 120 mL of acetone was added thereto. The resulting precipitate was taken out through filtration to be 9.88 g (25 mmol, yield 62%) of disilver ethane-1,2-disulfonate.

9.88 g (25 mmol) of the obtained disilver ethane-1,2-disulfonate was suspended in 100 mL of acetonitrile, then 7.00 g (59 mmol) of propargyl bromide was added thereto and refluxed at 82° C. for 6 hours. After the reaction, the reaction liquid was filtered, and the filtrate was concentrated under reduced pressure. The residue was recrystallized from dimethyl carbonate and hexane to give 3.88 g (yield 55%) of di(2-propynyl)ethane-1,2-disulfonate.

The $^1$H-NMR data of the obtained di(2-propynyl)ethane-1,2-disulfonate are shown below.

$^1$H-NMR (300 MHz, CDCl$_3$): δ=4.91 (d, J=2.4 Hz, 4H), 3.76 (s, 4H), 2.81 (t, J=2.4 Hz, 2H)

Examples II-1 to II-9, and Comparative Examples II-1 to II-2

(1) Production of Lithium Ion Secondary Battery

94% by mass of LiNi$_{1/3}$Mn$_{1/3}$CO$_{1/3}$O$_2$ (positive electrode active material) and 3% by mass of acetylene black (electroconductive agent) were mixed, and added to and mixed in a solution previously prepared by dissolving 3% by mass of polyvinylidene fluoride (binder) in 1-methyl-2-pyrrolidone, thereby preparing a positive electrode mixture paste. The positive electrode mixture paste was applied on one surface of an aluminium foil (collector), then dried, processed under pressure and cutted into a predetermined size, thereby producing a positive electrode sheet. The density of the part of the positive electrode except the collector was 3.6 g/cm$^3$. On the other hand, 95% by mass of artificial graphite (d$_{002}$=0.335 nm, negative electrode active material) was added to and mixed in a solution previously prepared by dissolving 5% by mass of polyvinylidene fluoride (binder) in 1-methyl-2-pyrrolidone, thereby preparing a negative electrode mixture paste. The negative electrode mixture paste was applied onto one surface of a copper foil (collector), dried, processed under pressure and cutted into a predetermined size, thereby producing a negative electrode sheet. The density of the part of the negative electrode except the collector was 1.7 g/cm$^3$. The positive electrode sheet, a porous polyethylene film separator and the negative electrode sheet were laminated in that order, and a nonaqueous electrolytic solution prepared by adding a predetermined amount of the alkyl sulfonates compound shown in Table 4 to the nonaqueous electrolytic solution having the composition also shown in Table 4 was added thereto to construct a 2032-type coin battery of Examples II-1 to II-9 and Comparative Examples II-1 to II-2.

(2) Evaluation of low-temperature cycle properties and (3) evaluation of high-temperature cycle properties were carried out according to the same method as in Example I-1.

(4) Evaluation of Storage Properties

In a thermostatic chamber kept at 25° C., the coin battery fabricated according to the above-mentioned method was charged up to a final voltage of 4.3 V for 3 hours with a constant current of 1 C and under a constant voltage, and then discharged to a final voltage of 3.0 V with a constant current of 1 C. The average discharging voltage during the discharging is the average discharging voltage before storage. Again this was charged up to a final voltage of 4.3 V for 3 hours with a constant current of 1 C and under a constant voltage, then put into a thermostatic chamber at 60° C., and while kept at 4.3 V, this was stored for 3 days. Subsequently, this was put into a thermostatic chamber at 25° C., then once discharged to a final voltage of 3.0 V under a constant current of 1 C, and again charged up to a final voltage of 4.3 V for 3 hours with a constant current of 1 C and under a constant voltage, and then discharged to a final voltage of 3.0 V under a constant current of 1 C. The average discharging voltage during the discharging is the average discharging voltage after storage. With that, a coin battery was fabricated in the same manner as in Example II-1 except that the alkynyl sulfonates compound represented by the general formula (III) was not added to the nonaqueous electrolytic solution therein, and evaluated for the battery characteristics as Comparative Example II-1. According to the formula mentioned below, as based on the value of the Comparative Example II-1, the average discharging voltage reduction rate after storage was calculated.

Average Discharging Voltage Reduction Rate (relative value) (%)=(average discharging voltage before storage−average discharging voltage after storage)/(average discharging voltage before storage in Comparative Example II-1−average discharging voltage after storage in Comparative Example II-1)×100.

The condition in producing the batteries and the battery characteristics are shown in Table 4.

Example II-10, Comparative Example II-3

A positive electrode sheet was produced by changing the positive electrode active material used in Example II-1 to LiFePO$_4$ coated with amorphous carbon (positive electrode active material). Concretely, 90% by mass of LiFePO$_4$ coated with amorphous carbon and 5% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a positive electrode mixture paste.

The positive electrode mixture paste was applied onto an aluminium foil (collector), dried, processed under pressure and cutted into a predetermined size, thereby producing a positive electrode sheet. Using the nonaqueous electrolytic solution having the composition shown in Table 5, coin batteries were produced and evaluated in the same manner as in Example II-1, except that the positive electrode sheet thus produced herein was used, that the charging final voltage was changed to 3.6 V and that the discharging final voltage was changed to 2.0 V. The results are shown in Table 5.

TABLE 4

| | Composition of Electrolyte Salt Composition of Nonaqueous Electrolytic Solution (ratio by volume of solvents) | Alkynyl Sulfonate Compound Represented by General Formula (III) or Comparative Compound | Added Amount *1 (% by mass) | 0° C. Discharge Capacity Retention Rate after 50 cycles (%) | 60° C. Discharge Capacity Retention Rate after 100 cycles (%) | Average Discharging Voltage Reduction Rate after high-temperature storage *2 (%) |
|---|---|---|---|---|---|---|
| Example II-1 | 1M LiPF6 EC/MEC/DMC (30/50/20) | 2-propynyl 2-(acetyloxy)ethanesulfonate | 0.05 | 72 | 77 | 72 |
| Example II-2 | 1M LiPF6 EC/MEC/DMC (30/50/20) | 2-propynyl 2-(acetyloxy)ethanesulfonate | 1 | 79 | 87 | 65 |
| Example II-3 | 1M LiPF6 EC/MEC/DMC (30/50/20) | 2-propynyl 2-(acetyloxy)ethanesulfonate | 8 | 77 | 85 | 74 |
| Example II-4 | 1M LiPF6 EC/MEC/DMC (30/50/20) | 2-propynyl 3-(methanesulfonyloxy)-propanesulfonate | 1 | 75 | 86 | 64 |
| Example II-5 | 1M LiPF6 EC/MEC/DMC (30/50/20) | 2-propynyl 3-(formyloxy)propane-sulfonate | 1 | 74 | 84 | 66 |
| Example II-6 | 1M LiPF6 EC/MEC/DMC (30/50/20) | 2-propynyl 2-methoxyethanesulfonate | 1 | 72 | 84 | 68 |
| Example II-7 | 1M LiPF6 EC/MEC/DMC (30/50/20) | 2-propynyl 3-(dimethoxyphosphoryloxy)-propanesulfonate | 1 | 71 | 83 | 70 |
| Example II-8 | 1M LiPF6 EC/MEC/DMC (30/50/20) | di(2-propynyl) ethane-1,2-disulfonate | 1 | 70 | 82 | 66 |
| Example II-9 | 1M LiPF6 FEC/VC/MEC/DMC (28/2/50/20) | 2-propynyl 2-(acetyloxy)ethanesulfonate | 1 | 82 | 89 | 61 |
| Comparative Example II-1 | 1M LiPF6 EC/MEC/DMC (30/50/20) | none | — | 64 | 66 | 100 |
| Comparative Example II-2 | 1M LiPF6 EC/MEC/DMC (30/50/20) | 2-butyne-1,4-diol dimethanesulfonate | 1 | 62 | 65 | 91 |

*1: content in nonaqueous electrolytic solution
*2: relative value

TABLE 5

| | Composition of Electrolyte Salt Composition of Nonaqueous Electrolytic Solution (ratio by volume of solvents) | Alkynyl Sulfonate Compound Represented by General Formula (III) | Added Amount *1 (% by mass) | 0° C. Discharge Capacity Retention Rate after 50 cycles (%) | 60° C. Discharge Capacity Retention Rate after 100 cycles (%) | Average Discharging Voltage Reduction Rate after high-temperature storage *2 (%) |
|---|---|---|---|---|---|---|
| Example II-10 | 1M LiPF6 EC/MEC/DMC (30/50/20) | 2-propynyl 2-(acetyloxy)-ethanesulfonate | 1 | 82 | 85 | 59 |
| Comparative Example II-3 | 1M LiPF6 EC/MEC/DMC (30/50/20) | none | 1 | 67 | 72 | 100 |

*1: content in nonaqueous electrolytic solution
*2: relative value

Example II-11, Comparative Example II-4

A negative electrode sheet was produced, using silicon (negative electrode active material) in place of the negative electrode active material used in Example II-1. Precisely, 80% by mass of silicon and 15% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a negative electrode mixture paste.

The negative electrode mixture paste was applied onto a copper foil (collector), dried, processed under pressure, and cutted into a predetermined size, thereby producing a negative electrode sheet. Using the nonaqueous electrolytic solution having the composition shown in Table 6, coin batteries were produced and evaluated in the same manner as in Example II-1, except that the negative electrode sheet produced herein was used. The results are shown in Table 6.

sulfonyl group (—S(=O)$_2$R) and a phosphoryl group (—P(=O)RR'), and a triple bond-having specific sulfonate group (—S(=O)$_2$OR) are bonded to each other via a hydrocarbon group optionally containing an oxygen atom at the terminal and/or in the intermediate thereof brings about the unexpected specific effect.

In addition, from comparison between Example II-10 and Comparative Example II-3, and from comparison between Example II-11 and Comparative Example II-4, the same effect is seen in the case where a lithium-containing olivine-type iron phosphate was used as the positive electrode, and in the case where Si was used as the negative electrode. Accordingly, it is known that the effect of the present invention does not depend on any specific positive electrode or negative electrode.

Further, the nonaqueous electrolytic solution of the present invention has an effect of improving the load characteristics after high-temperature storage of lithium primary batteries.

TABLE 6

| | Composition of Electrolyte Salt Composition of Nonaqueous Electrolytic Solution (ratio by volume of solvents) | Alkynyl Sulfonate Compound Represented by General Formula (III) | Added Amount *1 (% by mass) | 0° C. Discharge Capacity Retention Rate after 50 cycles (%) | 60° C. Discharge Capacity Retention Rate after 100 cycles (%) | Average Discharging Voltage Reduction Rate after high-temperature storage *2 (%) |
|---|---|---|---|---|---|---|
| Example II-11 | 1M LiPF6 EC/MEC/DMC (30/50/20) | 2-propynyl 2-(acetyloxy)-ethanesulfonate | 1 | 72 | 63 | 56 |
| Comparative Example II-4 | 1M LiPF6 EC/MEC/DMC (30/50/20) | none | 1 | 62 | 35 | 100 |

*1: content in nonaqueous electrolytic solution
*2: relative valu

The lithium secondary batteries of Examples II-1 to II-9 were all remarkably bettered in point of the load characteristics thereof after high-temperature charging storage since the average discharging voltage reduction after high-temperature storage thereof is small, as compared with the lithium secondary battery of Comparative Example II-1 (in which the compound of the present invention was not added), and Comparative Example II-2 (in which a compound having a triple bond in the chain of linking the two substituents therein was used). From the results, it is known that the structure in which two different substituents of one specific substituent selected from an ether group (—O—), a formyl group (—C(=O)H), an acyl group (—(C=O)R), a

INDUSTRIAL APPLICABILITY

The lithium secondary batteries using the nonaqueous electrolytic solution of the present invention are useful as electrochemical elements such as lithium secondary batteries excellent in low-temperature and high-temperature cycle properties and/or high-temperature charging storage properties.

In addition, the alkynyl compound represented by the general formula (II) is useful not only as an additive to electrochemical elements but also as an intermediate material for medicines, agricultural chemicals, electronic materials, polymer materials and others.

The invention claimed is:

1. An alkynyl compound having formula (I):

$$R^1(O)_n—X^1—R^2 \quad (I),$$

wherein
- $X^1$ is an —S(=O)$_2$— group;
- $R^1$ is an alkenyl group comprising from 2 to 8 carbon atoms;
- $R^2$ is an alkynyl group comprising from 3 to 8 carbon atoms or an alkynyloxy group comprising from 3 to 8 carbon atoms; and
- n is 0.

2. The alkynyl compound according to claim 1, wherein $R^2$ is an alkynyl group comprising from 3 to 8 carbon atoms.

3. The alkynyl compound according to claim 1, wherein $R^2$ is an alkynyloxy group comprising from 3 to 8 carbon atoms.

4. A nonaqueous electrolytic solution, comprising:
an electrolyte salt dissolved in a nonaqueous solvent; and
the alkynyl compound according to claim 1.

5. A nonaqueous electrolytic solution, comprising:
an electrolyte salt dissolved in a nonaqueous solvent; and
0.01% to 10% by mass, based on a total mass of the solution, of an alkynyl compound of formula (I):

$$R^1(O)_n—X^1—R^2 \quad (I),$$

wherein:
- $X^1$ is an —S(=O)$_2$— group;
- $R^1$ is an alkenyl group comprising from 2 to 8 carbon atoms;
- $R^2$ is an alkynyloxy group comprising from 3 to 8 carbon atoms;
and
- n is 0.

6. The solution of claim 5, wherein the alkynyl compound is 2-propynyl vinylsulfonate, 3-butynyl vinylsulfonate, 1,1-dimethyl-2-propynyl vinyl sulfonate, 2-propynyl 2-propene-1-sulfonate, 3-butynyl 2-propene-1-sulfonate, 1-methyl-2-propynyl 2-propene-1-sulfonate, 1,1-dimethyl-2-propynyl 2-propene-1-sulfonate or any mixture thereof.

7. The solution of claim 5, wherein the nonaqueous solvent comprises a cyclic carbonate.

8. An electrochemical element, comprising:
a positive electrode;
a negative electrode; and
the nonaqueous electrolytic solution of claim 5.

9. The solution of claim 7, wherein the cyclic carbonate is at least one selected from the group consisting of an ethylene carbonate, a propylene carbonate, a butylene carbonate and a cyclic carbonate comprising a carbon-carbon double bond or a fluorine atom.

10. The solution of claim 9, wherein the cyclic carbonate comprising a carbon-carbon double bond or a fluorine atom is at least one selected from the group consisting of a vinylene carbonate, a vinylethylene carbonate, a 4-fluoro-1,3-dioxolan-2-one, and a 4,5-difluoro-1,3-dioxolan-2-one.

11. The solution of claim 5, wherein the nonaqueous solvent comprises an asymmetric linear carbonate, a symmetric carbonate, or a mixture thereof, wherein:
the asymmetric linear carbonate is methyl ethyl carbonate, methyl propyl carbonate, methyl isopropyl carbonate, methyl butyl carbonate, ethyl propyl carbonate, or any mixture thereof; and
the symmetric carbonate is dimethyl carbonate, diethyl carbonate, dipropyl carbonate, dibutyl carbonate, or any mixture thereof.

12. The solution of claim 5, wherein the nonaqueous solvent comprises a linear ester, which is methyl propionate, ethyl propionate, methyl acetate, ethyl acetate, methyl pivalate, butyl pivalate, hexyl pivalate, octyl pivalate, dimethyl oxalate, ethyl methyl oxalate, or diethyl oxalate.

13. The solution of claim 5, wherein the nonaqueous solvent comprises a cyclic carbonate and a linear carbonate, and the volume ratio of cyclic carbonate/linear carbonate is from 10/90 to 40/60.

14. The solution of claim 5, wherein the electrolyte salt comprises LiPF$_6$, LiBF$_4$, LiN(SO$_2$CF$_3$)$_2$, LiN(SO$_2$C$_2$F$_5$)$_2$, or any mixture thereof.

15. The solution of claim 5, wherein a concentration of the electrolyte salt is from 0.3 M to 2.5 M.

16. The electrochemical element of claim 8, wherein the positive electrode comprises a lithium complex metal oxide, a lithium-containing olivine-type phosphate, or any mixture thereof.

17. The electrochemical element of claim 8, wherein the negative electrode comprises a lithium metal, a lithium alloy, a carbon material capable of absorbing and releasing lithium, a tin, a tin compound, a silicon, a silicon compound, or any mixture thereof.

18. The solution of claim 5, wherein the alkynyl compound is 2-propynyl vinylsulfonate or 1,1-dimethyl-2-propynyl vinylsulfonate.

19. The solution of claim 5, wherein the nonaqueous solvent comprises a cyclic carbonate comprising a fluorine atom, and the cyclic carbonate is included in an amount of from 4% by volume to 35% by volume, relative to a total volume of the nonaqueous solvent.

20. The solution of claim 5, wherein the nonaqueous solvent comprises methyl ethyl carbonate and dimethyl carbonate.

* * * * *